(12) United States Patent
Abbott et al.

(10) Patent No.: US 7,745,220 B2
(45) Date of Patent: Jun. 29, 2010

(54) DEVICES AND METHODS FOR ANALYTE DETECTION USING DISTORTED LIQUID CRYSTALS

(75) Inventors: Nicholas L. Abbott, Madison, WI (US); Brian H. Clare, Philadelphia, PA (US)

(73) Assignee: Wisconsin Alumni Research Foundation, Madison, WI (US)

(*) Notice: Subject to any disclaimer, the term of this patent is extended or adjusted under 35 U.S.C. 154(b) by 77 days.

(21) Appl. No.: 11/542,432

(22) Filed: Oct. 3, 2006

(65) Prior Publication Data

US 2010/0081123 A1 Apr. 1, 2010

Related U.S. Application Data

(60) Provisional application No. 60/723,100, filed on Oct. 3, 2005.

(51) Int. Cl.
*G01N 31/00* (2006.01)

(52) U.S. Cl. .................... 436/4; 436/164; 436/165; 436/180; 436/518; 436/532; 422/50; 422/52; 422/68.1; 422/73

(58) Field of Classification Search .......... 422/52, 422/50, 73, 68.1; 436/4, 164, 165, 180, 518, 436/528, 532
See application file for complete search history.

(56) References Cited

U.S. PATENT DOCUMENTS 6,075,512 A * 6/2000 Patel et al. .................. 345/101
6,284,197 B1 9/2001 Abbott
2002/0055093 A1 5/2002 Abbott
2004/0185551 A1 * 9/2004 Niehaus .................. 435/287.2

FOREIGN PATENT DOCUMENTS

WO WO02075294 9/2002

OTHER PUBLICATIONS

V.P. Vorflusev, H.S. Kitzerow, V.G. Chigrinov, "Azimuthal anchoring of liquid crystals at the surface of photo-induced anisotropic films", 1997, Appl. Phys. A, 64, 615-618.*
Tingey, M., et al., Langmuir, vol. 20, No. 16:6818-6826 (2004).
Tingey, M., et al., Advanced Materials, vol. 16, No. 15:1331-1336 (2004).
Gupta, V. K., et al., Science, vol. 279, No. 5359:2077-2080 (1998).

* cited by examiner

*Primary Examiner*—Lyle A Alexander
*Assistant Examiner*—Dennis M White
(74) *Attorney, Agent, or Firm*—Quarles & Brady LLP

(57) ABSTRACT

The present invention provides devices and methods for detection of analytes based on measuring the anchoring strength of liquid crystals having distorted geometries. Methods for detecting an analyte in a sample include the steps of: (a) capturing an analyte on a substrate surface wherein the substrate surface defines an easy axis when in contact with a liquid crystal. Substrate surface and liquid crystal are brought into contact and an analyte-dependent departure in the orientation of the liquid crystal from the easy axis of the substrate surface is measured. This departure indicates the presence of the analyte in the sample.

4 Claims, 28 Drawing Sheets

Equations used to convert δ and γ into φ and Ψ
1. Known values for δ and γ
2. Angle between polarizer P and $\eta_d$-top = γ - 90°
3. φ = δ - (γ - 90°)
4. Ψ = δ - 2φ

A

| Region | δ | φ | Ψ | W/K | W |
|---|---|---|---|---|---|
| 1 | 80.82 | 13.35 | 67.48 | 0.95 ± 0.09 | 4.02 ± 0.62 |
| 2 | 81.83 | 13.89 | 67.94 | 0.93 ± 0.09 | 3.90 ± 0.60 |
| 3 | 81.53 | 13.3 | 68.23 | 0.97 ± 0.09 | 4.08 ± 0.63 |
| 4 | 82.24 | 12.23 | 70.01 | 1.07 ± 0.10 | 4.53 ± 0.70 |
| 5 | 83.04 | 9.88 | 73.16 | 1.37 ± 0.13 | 5.80 ± 0.98 |
| 6 | 85.35 | 14.27 | 71.07 | 0.94 ± 0.09 | 3.98 ± 0.61 |

A

EG3-N: n = 3

EG4: n = 4

B

C

$X_{EG3-N} \approx X_{peptide}$

Equations used to convert δ and γ into φ and Ψ
1. Known values for δ and γ
2. Angle between polarizer P and $\eta_d$-top = γ - 90°
3. Ψ = γ - 90°
4. φ = δ - Ψ

| Peptide (μM) + antibody (nM) | γ | δ | φ | ψ | Waz/K22 (x 10⁶ /m) | Waz (μJ/m²) |
|---|---|---|---|---|---|---|
| EG4 | 164.9 | 84.9 | 9.9 | 74.9 | 1.27 | 5.3 |
| 0.01 (Y1173) + 100 | 163.6 | 83.7 | 10.1 | 73.6 | 1.23 | 5.19 |
| 0.01 (pY1173) + 0.01 | 161.8 | 83.4 | 11.6 | 71.8 | 1.05 | 4.43 |
| 0.01 (pY1173) + 0.1 | 159.4 | 81.6 | 12.2 | 69.4 | 0.97 | 4.09 |
| 0.01 (pY1173) + 1.0 | 153.5 | 81.3 | 17.8 | 63.5 | 0.63 | 2.65 |
| 0.01 (pY1173) + 10 | 145.3 | 78.8 | 23.5 | 55.3 | 0.43 | 1.81 |
| 0.01 (pY1173) + 100 | 139.9 | 78.3 | 28.4 | 49.9 | 0.34 | 1.43 |

D.

E.

DEVICES AND METHODS FOR ANALYTE DETECTION USING DISTORTED LIQUID CRYSTALS

CROSS-REFERENCE TO RELATED APPLICATION

The present utility patent application claims the benefit of U.S. Provisional 60/723,100, filed Oct. 3, 2005, which is incorporated by reference herein in its entirety.

STATEMENT REGARDING FEDERALLY SPONSORED RESEARCH

This invention was made with United States government support awarded by the National Science Foundation—Grant No. DMR-0079983 and National Institutes of Health—Grant No. 1 R01 CA108467-01. The United States has certain rights in this invention.

FIELD OF THE INVENTION

This invention relates generally to methods of analyte detection using liquid crystals. In particular, the present invention is directed to devices and methods for detection of analytes based on measuring the anchoring strength of liquid crystals having distorted geometries.

BACKGROUND OF THE INVENTION

In the absence of any external force, liquid crystals will align along the surfaces of samples with their optical axis along one direction, defined as the "easy axis" $\eta_0$. Conceptually, "anchoring strength" can be thought of as "the amount of force required to cause molecules in the LC at the interface to not lie along the easy axis of the sample." When the LC is contained between two surfaces which have their easy axes in two different directions, the LC is distorted, such as twisted, splayed or bent. In this distorted configuration, the LC is strained and has an elastic torque force (associated with the LC trying to minimize this strain) and partially "untwists", if the principle distortion is twist. As the distance between the two surfaces, d, gets smaller this elastic torque gets larger and larger, and the tendency of the liquid crystal to untwist, if the principle distortion is twist, will increase with decrease in d.

With surfaces that have infinitely strong anchoring energy, no amount of torque can cause the liquid crystal at the surface to slip away from the axes of the surfaces. In the case of the finite anchoring, as the elastic torque increases, the orientation of liquid crystal at the surface is dictated by the opposing forces of anchoring strength and elastic torque. The result is a compromised orientation that is $\phi$ away from the easy axis. One can estimate the anchoring strength of a surface based on the angle $\phi$ as a function of the distance between the two surfaces, d.

A variety of approaches have been explored for the control of the orientation of $\eta 0$, motivated by advancement in display technologies. The approaches include the oblique deposition of metals, metal oxides and organic materials; the use of mechanically sheared surfaces of organic and inorganic materials, the use of surfaces that are fabricated using photo- and nano-lithography. Many other methods are known by those skilled in the art to prepare surfaces that define an easy axis of a liquid crystal place Equally important for these devices is the ability to manipulate the strength of the interaction between substrate and LC, defined as anchoring energy $W_{az}$. The manipulation of azimuthal (in-plane) anchoring energy by tuning the rubbing parameters employed for the treatment of polymeric films is well-documented. However, the method of rubbing simultaneously introduces two elements of substrate structure that can influence LC behavior: 1) microgrooves, or anisotropic topography and 2) anisotropy in the orientation of polymer chains in the near-surface region. Several groups have isolated the contributions from topography, using surface gratings or hard skins that have feature sizes which can be systematically controlled. Conversely, the relationship between surface order and azimuthal anchoring strength has been studied independently of topography via the exposure of photo-alignment layers to linearly polarized light.

Related to the field of manipulation and measurement of azimuthal (in-plane) anchoring energy, the present invention utilizes liquid crystals in constrained geometries and, in certain aspects, offers increased sensitivity to the presence of bound analytes, and forms the basis of quantification of low levels of bound analytes.

SUMMARY OF THE INVENTION

In a first embodiment, the present invention provides a liquid crystal device. Such a liquid crystal device includes a reference surface that defines an easy axis when in contact with liquid crystal and a substrate surface that defines a second easy axis when in contact with liquid crystal. The substrate surface faces but is spaced apart from the reference surface and the easy axis of the substrate surface and the easy axis of the reference surface are rotated from one another by a known angle that is not zero. A captured analyte is present in or on the substrate surface. The device further includes a liquid crystal positioned between the reference surface and the substrate surface wherein the substrate surface and the reference surface are spaced a distance apart from each other such that the orientation of the liquid crystal at the substrate surface differs from the easy axis of the substrate surface by an angle that is greater than zero.

In preferred embodiments, a liquid crystal device according to the invention is configured with the reference surface and the substrate surface forming a wedge-shaped cavity in which is positioned the liquid crystal.

In certain embodiments, one or both of the reference surface and substrate surface are prepared using obliquely deposited films of metal, preferably, gold. As well, certain embodiments utilize a substrate surface comprising a patterned array. A variety of methods can be employed to create the pattern, including photolithography, soft lithography, microcontact printing, spotting, inkjet printing, affinity microcontact printing and microfluidics.

In preferred embodiments, the easy axis of the substrate surface and the easy axis of the reference surface are rotated from one another by a non-90 degree angle.

In certain embodiments, the reference and/or substrate surface includes a self-assembled monolayer, preferably a monolayer comprising an oligo (ethylene glycol).

Various liquid crystals may be utilized in the present invention including, but not limited to, the liquid crystal 4-cyano-4'-pentylbiphenyl (5CB). Other liquid crystals suitable for use in the invention include, but are not limited to, nematic liquid crystals (e.g., E7), smectic liquid crystals, thermotropic liquid crystals, lyotropic liquid crystals, polymeric liquid crystals, cholesteric liquid crystals and ferroelectric liquid crystals.

The captured analyte included in or on the substrate surface may be a biomolecule or a synthetic molecule and is, preferably, a protein or nucleic acid. Biomolecules suitable as captured analytes include, but are not limited to, receptors or ligands. In alternative embodiments, the captured analyte may also be a toxic chemical, chemical warfare agent, a eukaryotic or prokaryotic cell, or an assembly of biomolecules such as a protein aggregate, a virus, yeast cell or plankton, or it may be a sugar, a lipid or phospholipid or glycolipid. The analyte may be captured through the presence of a binding group on the surface, or the analyte may be deposited into the surface or adsorbed in the absence of a binding group. The analyte may also be a biomolecule or synthetic molecule that has been transformed in structure through a chemical reaction or physical interaction, and the invention in this embodiment may provide a means to report the transformation of the analyte, that it is the state of the analyte rather than just the presence of the analyte.

In another embodiment, the present invention is directed to a method for forming a liquid crystal device. Such a method includes steps of: (a) assembling: (i) a reference surface that defines an easy axis when in contact with liquid crystal; and (ii) a substrate surface that defines a second easy axis when in contact with liquid crystal. The substrate surface faces but is spaced apart from the reference surface and the easy axis of the substrate surface and the easy axis of the reference surface are rotated from one another by a known angle that is not zero. A captured analyte is present in or on the substrate surface. A liquid crystal is provided between the reference surface and the substrate surface wherein the substrate surface and the reference surface are spaced a distance apart from each other such that the orientation of the liquid crystal at the substrate surface differs from the easy axis of the substrate surface by an angle that is greater than zero. The diversity of analytes reported by this method is described above and includes biomolecules such as proteins and nucleic acids as well as assemblies of biomolecules such as viruses and organisms. It also includes synthetic molecules, such as surfactants and pesticides, and it also includes ions such as heavy metal ions.

In preferred embodiments, the reference surface and the substrate surface are configured to form a wedge-shaped cavity in which is positioned the liquid crystal.

The present invention also encompasses a method for detecting an analyte in a sample. Such a method includes steps of: (a) assembling: (i) a reference surface that defines an easy axis when in contact with liquid crystal; and (ii) a substrate surface that defines a second easy axis when in contact with liquid crystal and faces but is spaced apart from the reference surface. The easy axis of the substrate surface and the easy axis of the reference surface are rotated from one another by a known angle that is not zero. A captured analyte is present in or on the substrate surface. A liquid crystal is then introduced between the reference surface and the substrate surface wherein the substrate surface and the reference surface are spaced a distance apart from each other such that the orientation of the liquid crystal at the substrate surface differs from the easy axis of the substrate surface by an angle that is greater than zero. An analyte-dependent departure of the orientation of the liquid crystal from the easy axis of the substrate surface is then measured with the departure indicating the presence of the analyte in the sample.

In preferred methods, the reference surface and the substrate surface form a wedge-shaped cavity in which is positioned the liquid crystal. The captured analyte may be a biomolecule or a synthetic molecule and is, preferably, a protein or nucleic acid. Biomolecules suitable as captured analytes include, but are not limited to, receptors or ligands. In alternative embodiments, the captured analyte may also be a toxic chemical or chemical warfare agent.

In another embodiment, the invention is directed to another method for detecting an analyte in a sample. Such a method includes steps of capturing an analyte on a substrate surface where the substrate surface defines an easy axis when in contact with liquid crystal. The substrate surface is then contacted with a liquid crystal and an analyte-dependent departure in the orientation of the liquid crystal from the easy axis of the substrate surface is measured, the departure indicating the presence of the analyte in the sample.

The present invention also encompasses a method for detecting an analyte in a sample that includes steps of (a) capturing an analyte on an interface formed between an aqueous phase and a droplet comprised by a liquid crystal; and (b) measuring an analyte-dependent change of the orientation of the liquid crystal measured relative to the easy axis of the droplet. The departure indicates the presence of the analyte in the sample.

Other objects, features and advantages of the present invention will become apparent after review of the specification, claims and drawings.

DETAILED DESCRIPTION OF THE INVENTION

I. In General

Figure 1:
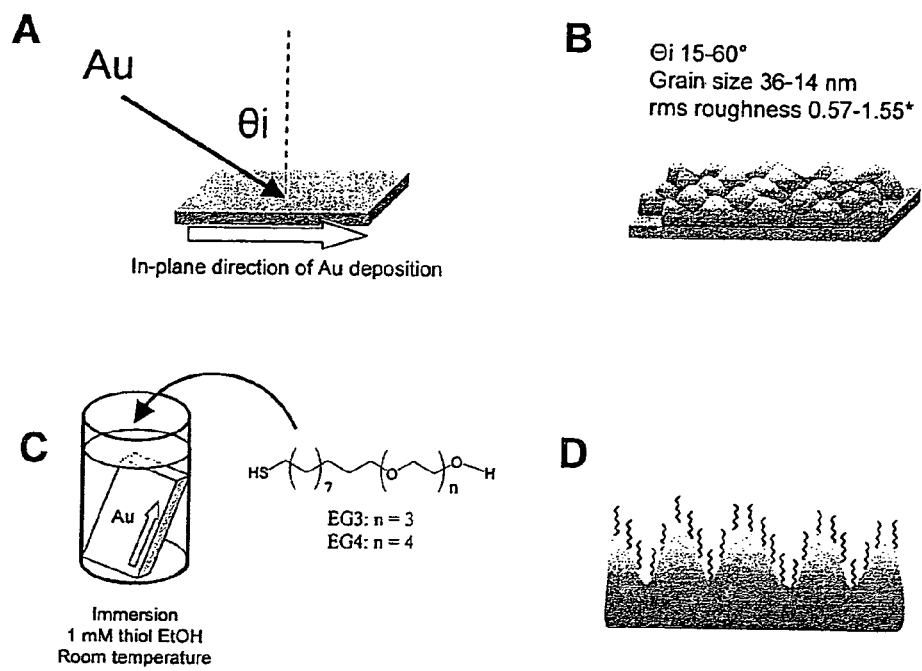
FIG. 1A depicts self-assembled monolayers (SAMs) supported on metal films prepared by the vapor deposition of gold at oblique (grazing) angles of incidence ($\theta i$, measured from the surface normal); B, substrates designed with systematic control of topography; C, schematic of SAM fabrication; D, the in-plane ordering of organosulfur species chemisorbed from solution.

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the materials, chemicals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

II. The Invention

In a first embodiment, the present invention provides a liquid crystal device useful for analyte detection. Such a liquid crystal device includes a reference surface that defines an easy axis when in contact with liquid crystal and a substrate surface that defines a second easy axis when in contact with liquid crystal. The substrate surface faces but is spaced apart from the reference surface and the easy axis of the substrate surface and the easy axis of the reference surface are rotated from one another by a known angle that is not zero. A captured analyte or deposited reagent is present in or on the substrate surface. The device further includes a liquid crystal positioned between the reference surface and the substrate surface wherein the substrate surface and the reference surface are spaced a distance apart from each other such that the orientation of the liquid crystal at the substrate surface differs from the easy axis of the substrate surface by an angle that is greater than zero.

In preferred embodiments, a liquid crystal device according to the invention is configured with the reference surface and the substrate surface forming a wedge-shaped cavity in which is positioned the liquid crystal.

The "distance" defining the length of the space between the reference surface and the substrate surface needed to cause the liquid crystal to differ in orientation from the easy axis of the substrate surface may be determined, for example, by the particular methodology and equations taught in Example 1 below, namely, the determination of d in the torque balance equation $(\Psi K/d)=(W \sin 2\phi)/2$. The "distance" aspect described and claimed herein relates to the measurement of azimuthal anchoring energy of liquid crystal. The "distance" d can be calculated for any liquid crystal for which the other variables in the torque balance equation are available, e.g. from the manufacturer or from empirical determination. Prior liquid crystal devices were not designed to measure anchoring energy of liquid crystal and, accordingly, the "distance" aspect key to measurement of anchoring energy was not a consideration in their design choice.

In certain embodiments, one or both of the reference surface and substrate surface are prepared using obliquely deposited films of metal, preferably, gold. As well, certain embodiments utilize a substrate surface comprising a patterned array.

In preferred embodiments, the easy axis of the substrate surface and the easy axis of the reference surface are rotated from one another by a non-90 degree angle.

As used herein, the term "strong anchoring" refers to combinations of surfaces and liquid crystals that have an anchoring energy that is sufficiently large that the orientation of the liquid crystal coincides with the easy axis. Under conditions of strong anchoring, the presence of a deformation in the bulk of a liquid crystal will not lead to a change in the orientation of the liquid crystal at the surface. Suitable materials for fabrication of reference and substrate surfaces capable of providing strong anchoring when used in combination with the liquid crystals described herein include, but are not limited to self-assembled monolayers formed from alkanethiols, including pentadecanethiol, rubbed polyimide films, rubbed polymer films, rubbed protein films, silane monolayers, organosulfur containing monolayers, alignment layers for liquid crystals that are prepared using polarized light, nanofabricated surfaces, silicon oxides, materials deposited by chemical and physical vapor deposition and microfabricated surfaces prepared using photolithography (see, e.g., I. Dozov et al., *Applied Physics Letters* 77, Issue 25, pp. 4124-4126 (2000); Faetti et al., *Phys Rev. E* 72, 051708 (2005); Brown et al., *Liquid Crystals* 27, pp. 233-242 (2000), all incorporated herein by reference). In certain preferred embodiments, the surfaces are oligo(ethylene glycol)-terminated SAMs provided on obliquely deposited gold films. Examples provided below demonstrate that gold film morphology and monolayer structure can be used to manipulate anchoring energy strengths to provide suitable strong anchoring surfaces for use in the invention.

Various liquid crystals may be employed with the above-described strong anchoring surfaces in the devices and methods of the present invention. Examples of suitable liquid crystals, include, but are not limited to, 4-cyano-4'-pentylbiphenyl (5CB), 7CB, and 8CB. A large listing of suitable liquid crystals is presented in "Handbook of Liquid Crystal Research" by Peter J. Collings and Jay S. Patel, Oxford University Press, 1997, ISBN 0-19-508442-X. Polymeric liquid crystals are also suitable for use in the device and methods of the present invention. Other liquid crystals are nematic liquid crystals such as E7, smectic liquid crystals, thermotropic liquid crystals, lyotropic liquid crystals, polymeric liquid crystals, cholesteric liquid crystals and ferroelectric liquid crystals. In one embodiment of the present invention, the liquid crystal deposited in the device is 4-cyano-4'-pentylbiphenyl (5CB). Although various types of liquid crystal may be employed, nematic and thermotropic liquid crystals are preferred. However, smectic liquid crystals formed from 8CB are also suitable for use in the present invention. Suitable liquid crystals further include smectic C, smectic C*, blue phases, cholesteric phases, smectic A, and polymeric liquid crystals. It is further envisioned that LCs useful in the invention may further include additions of dopants such as, but not limited to, chiral dopants as described by shiara H, et al. (*Chemistry Letters* 3: 261-262 (1998)) and Pape, M., et al. (*Molecular Crystals and Liquid Crystals* 307: 155-173 (1997)). Such dopants provide the further advantage of introducing into the liquid crystals a tendency to spontaneously assume a distorted state, such as a twisted state in the case of the addition of a chiral dopant to a nematic liquid crystals. The introduction of the dopant will permit manipulation of the torque transmitted to the surface by the liquid crystals and thus permit manipulation of the range of anchoring energies that can be measured using this invention. Other dopants, such as salts, will permit manipulation of the electrical double layers that form at the interfaces of the liquid crystals and thus permit manipulation of the strength of the anchoring of the liquid crystal at the interfaces.

The captured analyte included in or on the substrate surface may be a biomolecule or a synthetic molecule and is, preferably, a protein or nucleic acid. The diversity of analytes reported by this method is described above and includes biomolecules such as proteins and nucleic acids as well as assemblies of biomolecules such as viruses and organisms. Biomolecules suitable as captured analytes include, but are not limited to, receptors or ligands. It also includes synthetic molecules, such as toxic chemicals, chemical warfare agents, surfactants, herbicides and pesticides, and it also includes ions such as heavy metal ions. In alternative embodiments, the analyte is a eukaryotic or prokaryotic cell, or an assembly of biomolecules such as a protein aggregate, a virus, yeast cell or plankton, or it may be a sugar, a lipid or phospholipid or glycolipid. The analyte may be captured through the presence of a binding group on the surface, or the analyte may be deposited into the surface or adsorbed in the absence of a binding group. The analyte may also be a biomolecule or synthetic molecule that has been transformed in structure through a chemical reaction or physical interaction, and the invention in this embodiment may provide a means to report the transformation of the analyte, that it is the state of the analyte rather than just the presence of the analyte (see, e.g., Example 4 directed to the detection of phosphor-tyrosine residues). Accordingly, chemical entities differing in, for example, oxidation state or phosphorylation state may be selectively detected by the present invention. In other embodiments of the invention the analytic may adsorb onto the liquid crystals from an aqueous phase, the forming a layer at the interface between the aqueous phase and liquid crystal. For example, the analyte can be a phospholipid or a polyelectrolyte. In certain embodiments, the captured analyte is transferred to the substrate surface by affinity contact printing as described in U.S. patent application Ser. No. 10/711,517, filed Sep. 23, 2004, incorporated herein by reference.

In another embodiment, the present invention is directed to a method for forming a liquid crystal device. Such a method includes steps of: (a) assembling: (i) a reference surface that defines an easy axis when in contact with liquid crystal; and (ii) a substrate surface that defines a second easy axis when in contact with liquid crystal. The substrate surface faces but is spaced apart from the reference surface and the easy axis of the substrate surface and the easy axis of the reference surface are rotated from one another by a known angle that is not zero. A captured analyte is present in or on the substrate surface. A liquid crystal is provided between the reference surface and the substrate surface wherein the substrate surface and the reference surface are spaced a distance apart from each other such that the orientation of the liquid crystal at the substrate surface differs from the easy axis of the substrate surface by an angle that is greater than zero. It is preferred that at least the reference surface provides for strong anchoring interactions with the liquid crystal.

In preferred embodiments, the reference surface and the substrate surface are configured to form a wedge-shaped cavity in which is positioned the liquid crystal. Methods according to the invention may also include the step of transferring analyte to the substrate surface from a functionalized stamp. Accordingly, the captured analyte may be provided by affinity micro-contact printing.

The present invention also encompasses a method for detecting an analyte in a sample. Such a method includes steps of: (a) assembling: (i) a reference surface that defines an easy axis when in contact with liquid crystal; and (ii) a substrate surface that defines a second easy axis when in contact with liquid crystal and faces but is spaced apart from the reference surface. The easy axis of the substrate surface and the easy axis of the reference surface are rotated from one another by a known angle that is not zero. A captured analyte is present in or on the substrate surface. In certain embodiments, the captured analyte is transferred to the substrate surface by affinity micro-contact printing. A liquid crystal is then introduced between the reference surface and the substrate surface wherein the substrate surface and the reference surface are spaced a distance apart from each other such that the orientation of the liquid crystal at the substrate surface differs from the easy axis of the substrate surface by an angle that is greater than zero. An analyte-dependent departure of the orientation of the liquid crystal from the easy axis of the substrate surface is then measured with the departure indicating the presence of the analyte in the sample.

In preferred methods, the reference surface and the substrate surface form a wedge-shaped cavity in which is positioned the liquid crystal. The captured analyte may be a biomolecule or a synthetic molecule and is, preferably, a protein or nucleic acid. Biomolecules suitable as captured analytes include, but are not limited to, receptors or ligands. In alternative embodiments, the captured analyte may also be a toxic chemical or chemical warfare agent.

In another embodiment, the invention is directed to yet another method for detecting an analyte in a sample. Such a method includes steps of capturing an analyte on a substrate surface where the substrate surface defines an easy axis when in contact with liquid crystal. The substrate surface is then contacted with a liquid crystal and an analyte-dependent departure in the orientation of the liquid crystal from the easy axis of the substrate surface is measured, the departure indicating the presence of the analyte in the sample.

The present invention further encompasses methods of fabricating and using LC droplets to detect the presence of an analyte in a sample. In certain embodiments, anchoring energy measurements are obtained from LC-polyelectrolyte multilayer droplets. In short, LC-in-water emulsions are formed by sonicating a mixture of liquid crystal, preferably 5CB, in an aqueous solution of a strongly charged polyelectrolyte, (e.g., poly(styrene sulfonate) (PSS)). The LC droplets are spherical and may be separated into populations comprised of various diameters by sedimentation. Layer-by-layer assembly is then carried out to deposit alternating charged layers, e.g. polyallyamine hydrochloride (PAH) and PSS. The optical appearance of the LC is then recorded by using polarized light microscopy. Next, an analyte that interacts with the PEM and/or liquid crystal is introduced into the system. The optical appearance of the droplets is observed using the polarized light microscope. It is observed that the optical appearance of the droplets changes in a manner that depends on the size of the LC droplets. By recording the time at which droplets change their optical appearance, a method to quantify the concentration of analyte in solution is established. The transition time and orientation of the LC is influenced by the anchoring energy of the LC at the surface of the droplets and the elastic energy stored in the LC confined within the droplet. Suitable LCs for use in droplet-related techniques are previously-mentioned herein. Past studies have established that the orientations of a LC within a droplet depend on factors such as the bulk elasticity of the LC, the orientation of the easy axis of the LC at the interface of the droplet, and the anchoring energy of the LC. For sufficiently large droplets, surface anchoring dominates, which results in droplets that contain topological defects at equilibrium. The key governing equation can be understood as resulting from a competition between surfaces effects, which is proportional to $W_a R^2$, where Wa is the anchoring energy and R is the droplet radius, and a bulk elastic energy associated with the distortion of the liquid crystal within the droplet, which is proportional ato KR, where K is an elastic constant. When the energy associated with the distortion in the bulk of the droplet is much greater than the surface anchoring energy, the droplet will tend towards a uniform orientation in the bulk of the droplet; on the other hand, when the surface anchoring energy is large compared to the bulk elastic energy, the liquid crystal will tend to assume the easy axis at the surface of the droplet and the liquid crystal within the bulk of the droplet will be distorted. The critical size of the droplet where the surface and bulk effects are in balance is given approximately by the radius where WaR2=KR.

Materials that can be used in combination with droplets includes analytes that will assemble or can be deposited on the surface of the droplets, including surfactants, lipids, amphiphilic polymers, proteins, nucleic acids, peptide amphiphiles, glycolipids, polyelectrolytes. In preferred embodiments it is also possible to assemble complex mixtures such as cell membrane extracts, cell lysates, tissue homogenates, components of serum on the interfaces of the liquid crystal. Accordingly, LC droplets provide a useful means to detect the presence of an analyte in a sample.

The following examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

III. EXAMPLES

Example I

Manipulating the Azimuthal Anchoring Strength of Liquid Crystals in Contact with Oligo(ethylene glycol)-Terminated Self-Assembled Monolayers Supported on Obliquely Deposited Gold Films In this example, the inventors provide an approach for the manipulation of anchoring energy, using self-assembled monolayers (SAMs) supported on metal films prepared by the vapor deposition of gold at oblique (grazing) angles of incidence (θi, measured from the surface normal), as shown in FIG. 1A. This class of substrates can be designed with systematic control of topography (FIG. 1B) and the in-plane ordering of organosulfur species chemisorbed from solution (FIGS. 1C and 1D). Additionally, the choice of the terminal group allows one to choose the nature of the interaction between substrate and the LC, such as hydrogen-bonding, van der Waals, or electrostatics.

Oligo(ethylene glycol)-terminated SAMs (EGX SAMs) on gold films form the basis of functional surfaces for biosensing applications, as they are known to resist the nonspecific adsorption of proteins and lead to high selectivity in the detection of a target analyte. The inventors have demonstrated control of the orientations of LCs in contact with EGX SAMs (structures shown in FIG. 1C) supported on obliquely deposited gold, and exploited the surface sensitivity of LC to amplify and report protein binding events occurring on EGX SAMs.

Figure 2:
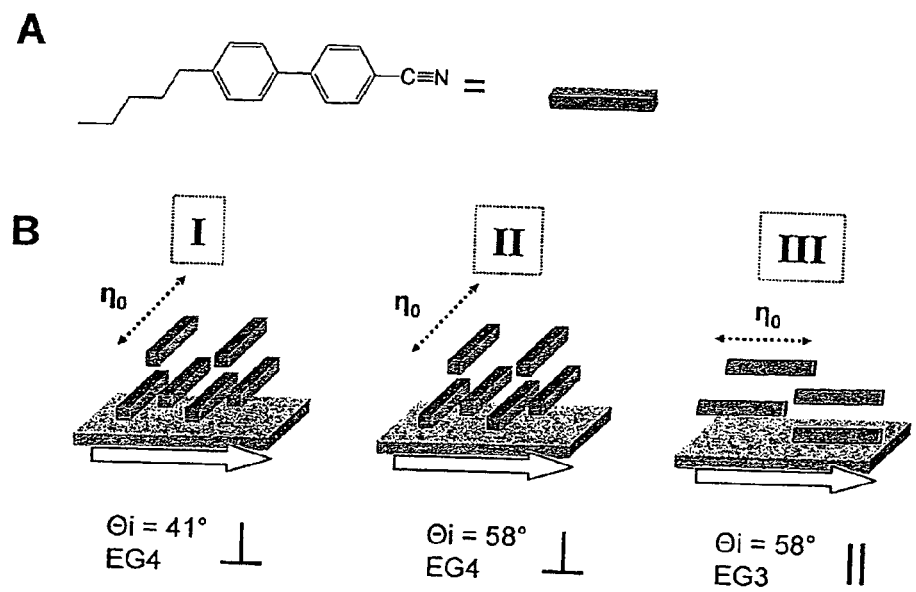
FIG. 2A illustrates the chemical structure of nematic liquid crystal (LC) 4-cyano-4'-pentylbiphenyl; B, 5CB in contact with three substrates.
Figure 3:
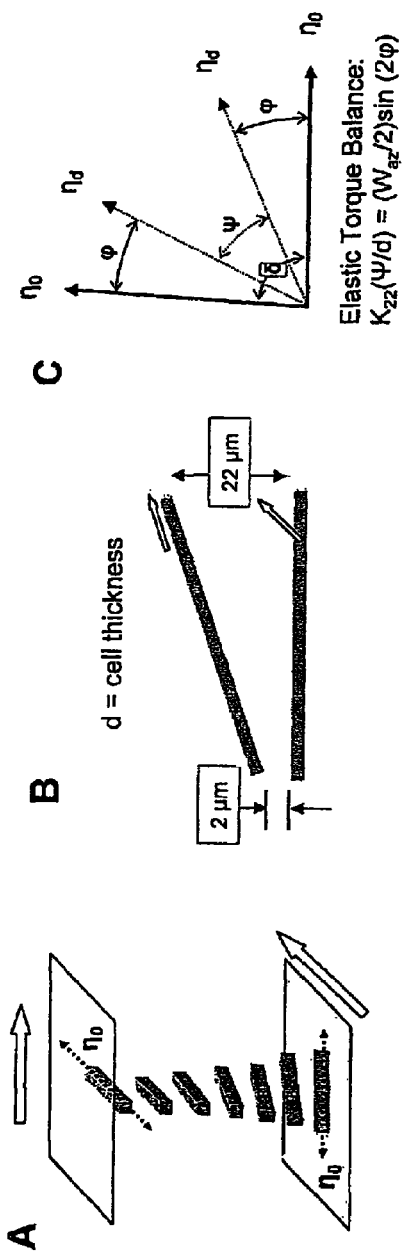
FIG. 3A shows two identically-treated substrates used to confine the LC, arranged such that the easy axes $\eta_0$ are oriented orthogonally; B, surfaces are spaced apart in a wedge-shaped geometry, such that the film thickness varies across the sample; C, for sufficiently thin LC films, the bulk elastic torque of the twist distorted LC competes with the surface anchoring torque, resulting in an equilibrium orientation of the director at $\eta_d$.

The inventors investigated the azimuthal anchoring energy of the nematic liquid crystal 4-cyano-4'-pentylbiphenyl (5CB, depicted in FIG. 2A) in contact with three substrates, shown in FIG. 2B, that are prepared by systematically changing the topography (Case I to II) and molecular-level structure of SAM (Case II to III). The technique used to measure the azimuthal anchoring energies for each substrate is based on the elastic torque-balance model using liquid crystals in twisted geometries. Two identically-treated substrates are used to confine the LC, and are arranged such that the easy axes $\eta_0$ are oriented orthogonally (FIG. 3A). The surfaces are spaced apart in a wedge-shaped geometry, such that the film thickness varies across the sample (FIG. 3B). For sufficiently thin LC films, the bulk elastic torque of the twist distorted LC competes with the surface anchoring torque, resulting in an equilibrium orientation of the director at $\eta_d$ (FIG. 3C). The two confining surfaces are identical, so this deviation occurs equally at each interface. The angle of deviation $\phi$ and geometrical twist of the LC $\Psi$ can be measured using an optical method where patterned SAMs are used to determine the angle formed between n0 for the top and bottom surfaces (see further details below).

Materials and Methods

Materials. All materials were used as received unless otherwise noted. Fisher's Finest glass slides were obtained from Fisher Scientific (Pittsburgh, Pa.). Gold 99.999% purity was obtained from International Advanced Materials (Spring Valley, N.Y.). Titanium 99.99% purity was obtained from PureTech (Brewster, N.Y.). Liquid crystal 4-cyano-4'-pentylbiphenyl (5CB) was obtained from EM Industries (New York, N.Y.) sold under the trademark name Licristal® (K15). Oligo (ethylene glycol)-terminated thiols were synthesized using previously published methods. Ethanol (200-proof) was obtained from Aaper Alcohol (Shelbyville, Ky.) and purged at least 1 hour with argon gas prior to use. Polydimethylsiloxane (PDMS) elastomeric stamps were prepared using Sylgard® 184 silicone elastomer kit obtained from Dow Corning (Midland, Mich.).

Preparation of Gold Substrates. Glass Slides were First Cleaned Using a Piranha solution as outlined in a prior publication. The slides were then positioned within the chamber of an electron beam evaporator such that the incidence angle of metal vapor flux to the substrate (defined with respect to the surface normal) could be controlled. The incident angles were measured manually using a digital level, with an accuracy of ±2°. All metal films were deposited at chamber pressures <1×10-6 ton and at deposition rates of <0.2 Å/s. First, a thin film of titanium (total thickness of 42-60 Å) was deposited onto the glass substrate to serve as an adhesion layer. Next, semi-transparent films of gold (total thickness 105-140 Å) were deposited onto the substrate. These substrates will be referred to as "obliquely deposited gold films". All gold substrates were used within 1 hour of removal from the evaporator chamber.

Formation of patterned self-assembled monolayers (SAMs). First, a polydimethylsiloxane (PDMS) elastomeric stamp with feature widths of 2-3 mm pitch and 2-3 mm height was cast from an aluminum master. The stamp was inked with a 1 mM ethanolic solution of either pentadecanethiol or hexadecanethiol, then gently dried using a stream of nitrogen gas. The stamp was placed in contact with the obliquely deposited gold film for 5-10 seconds. Next, 1 mM solutions of oligo (ethylene glycol)-terminated thiols were prepared using argon purged ethanol. These solutions were stored under an argon atmosphere to prevent oxidation of the sulfhydryl functionality. The gold substrates were next immersed into the thiol solutions for 18 hours, and then rinsed with copious amounts of water and ethanol, and then gently dried under a stream of nitrogen gas prior to placing them in contact with 5CB.

Preparation of Optical Cell Having Wedge-Shaped Geometry. Two Identically-treated substrates of interest were placed face-to-face, such that in-plane direction of gold deposition of the bottom surface was rotated approximately 90° relative to the in-plane direction of gold deposition of the top surface (Shown in FIG. 3A). The surfaces were separated by a 22 μm spacer at one end, and were not separated by a spacer at the other end, to create a wedge-shaped cell (Shown in FIG. 3B). The optical cell, and 5CB, were both warmed to approximately 40-45° C. (above the clearing point for 5CB). 5CB was then drawn into the optical cell by capillary action and slowly cooled to room temperature. Measurements of the optical properties of the LC film for all samples were taken after 30 minutes of cooling to room temperature (22° C.), as both temperature and age of the sample (surface gliding) are known to influence the measured anchoring strength.

Optical determination of d, δ, Ψ and φ. Measurements were taken using a polarized light microscope (BX 60, Olympus) equipped with an X-Y translating stage and fitted with a digital camera for image capture. Methods to determine the thickness and optical properties of the film were adapted from methods published by Fonseca and Galerne (Fonseca, J. G.; Galerne, Y. *Appl. Phys. Lett.* 2001, 79, 2910), as described herein.

Results

Figure 4:
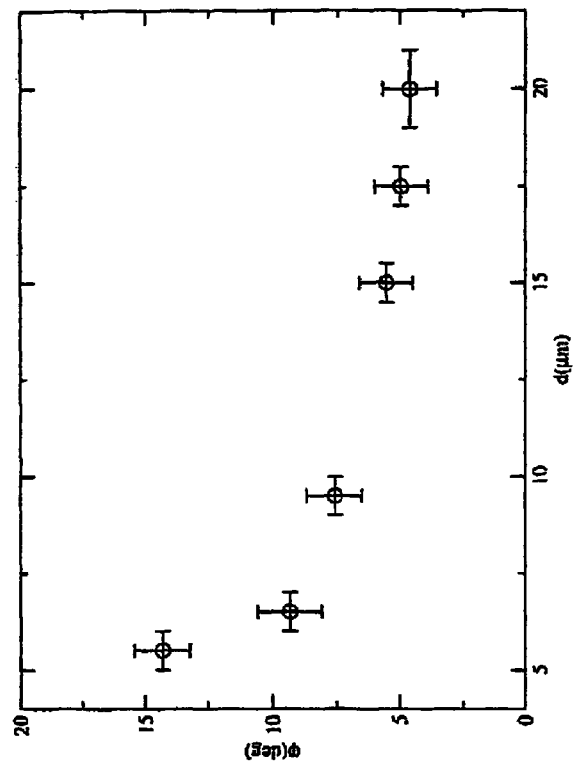
FIG. 4 illustrates the behavior of $\phi$ as a function of cell thickness for the specific case of EG4 SAM on oblique gold ($\theta i=58°$).

Using the optical method described by Fonseca and Galerne, the inventors determined 1) φ (deviation of director $\eta_d$ from the easy axis $\eta_0$), and 2) Ψ (twist of the liquid crystal) for each set of substrates depicted in FIG. 3C as a function of thickness. For clarity, the inventors describe the behavior of φ as a function of cell thickness for the specific case of EG4 SAM on oblique gold ($\theta i=58°$), shown in FIG. 4. It was identified that as the film thickness (d) decreases, the equilibrium position of the director deviates at a larger angle from the easy axis. Conversely, as the film thickness increases, the equilibrium position of the director lies more closely along the easy axis $\eta_0$. This observed behavior is expected, as the bulk elastic torque (which causes the deviation) is inversely proportional to d. The inventors found that when using very thick films (d≧50 μm), the deviation φ approaches zero (data not shown). Error bars in the y-direction reflect uncertainty in the measurement of the two angles used to determine φ (±0.5°), and error bars in the x-direction reflect uncertainty in thickness measurements. It was observed that the optical method used to determine φ (and Ψ) is only valid for films of sufficient thickness, in the Mauguin waveguide regime and measurements were taken at thicknesses >6 μm.

Figure 5:
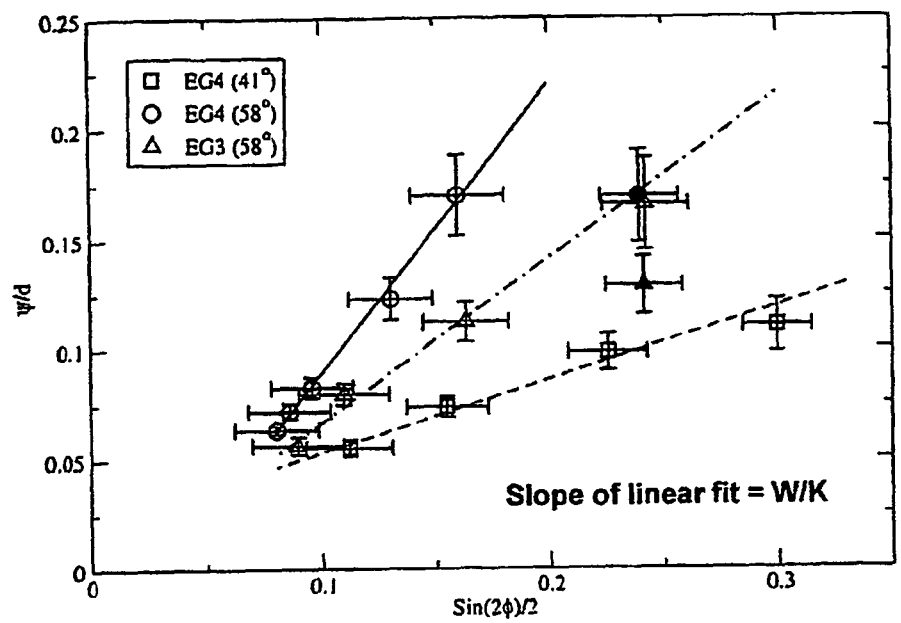
FIG. 5A shows a ($\Psi/d$) vs. ($\sin 2\phi$)/2 plot for each set of substrate conditions (Cases I-III). The error bars in the x- and y-direction for each data point reflect uncertainties in the measurements of thickness d and of the angles used to calculate $\Psi$ and $\phi$; B, a table displaying the calculated azimuthal anchoring energy $W_{az}$ for each set of substrate conditions (see Example 2)

To estimate W, the inventors first fit data according to the torque balance equation: $(\Psi K/d)=(W \sin 2\phi)/2$. For each set of substrate conditions (Cases I-III), the inventors plotted $(\Psi/d)$ vs. $(\sin 2\phi)/2$, as shown in FIG. 5A. The error bars in the x- and y-direction for each data point reflect uncertainties in the measurements of thickness d and of the angles used to calculate Ψ and φ. For some points, the y-axis error bar is small enough that it fits within the data point. A linear fit of this data will have a slope equal to the ratio W/K. Linear fits of each data set was subjected to a $\chi^2$ test, and each fit was acceptable with a significance level of 95%. Using a measured value for K22 at 22° C. taken from the literature (Toyooka, T.; Chen, G.-P.; Takezoe, H.; Fukuda, A. *Jpn. J. Appl. Phys.* 1987, 26, 1959), the inventors calculated the azimuthal anchoring energy $W_{az}$ for each set of substrate conditions, as summarized in FIG. 5B.

The inventors describe in this example azimuthal anchoring energy measurements made for a nematic liquid crystal in contact with self-assembled monolayers (of any structure) supported on obliquely deposited gold films. In the context of obliquely deposited films of SiO ($W_{az}$ for 5CB reported to be $>10^{-5}$ J/m² at room temperature) the anchoring on obliquely deposited gold is weak.

It is shown herein that self-assembled monolayers supported on obliquely deposited gold films are interfaces that can be systematically changed to manipulate azimuthal anchoring energies. Both the morphology of the supporting gold film and the molecular-level structure of the monolayer influence the magnitude of anchoring strength. Second, these results can be used to support the inventors' observations that the manipulation of these substrates leads to changes in the sensitivity of LC in reporting protein binding events. Third, this example illustrates how the optical behavior of twisted nematic liquid crystals, as demonstrated here, can be interpreted as a measure of very subtle differences in interfacial structure. Accordingly, this strategy is applicable in reporting structural changes as a result of biomolecular binding events.

The following information is supplemental to the above-provided disclosure and included to ensure a thorough description of the subject matter described and claimed herein. As noted above, this example illustrates the preparation and analysis of twisted nematic liquid crystals for the determination of azimuthal anchoring energies using the torque balance method. The description of the method is organized into four parts: 1) sample preparation, 2) determination of cell thickness d, 3) determination of δ and 4) determination of Ψ and φ. For consistency, all of the examples shown were used for the analysis of the anchoring energy of 5CB in contact with EG4 on oblique gold prepared using a deposition angle of θi=58°.

Figure 6:
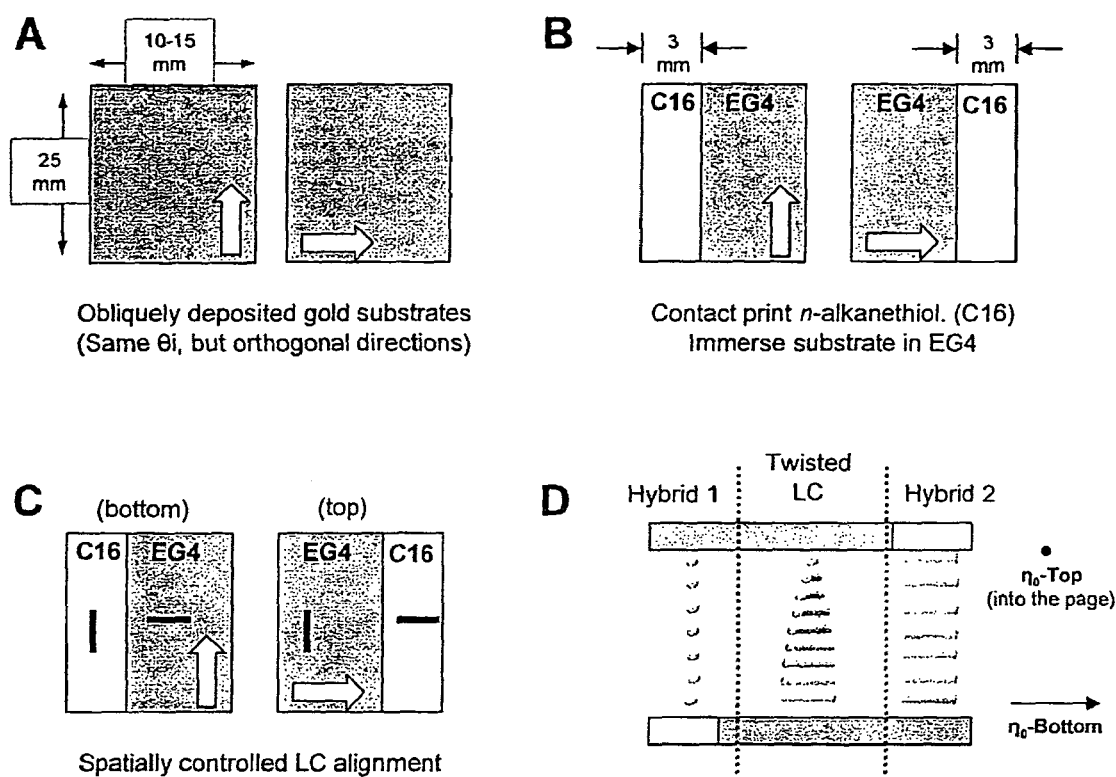
FIG. 6A depicts the preparation of two obliquely deposited gold films with deposition angle $\theta i$ (the direction of gold deposition depicted as white arrow); B, a polydimethylsiloxane (PDMS) elastomer was used to contact print defined regions of hexadecanethiol onto each substrate. The entire substrate was then immersed into a 1 mM ethanolic solution of the EG4 thiol at room temperature for a pre-determined length of time, then rinsed with copious amounts of water and ethanol, and dried gently using a stream of nitrogen gas; C, 5CB will orient such that the easy axis, $\eta_0$ (depicted as black bar), on EG4 SAM is perpendicular to the direction of gold deposition; D, finally, the two SAMs are placed face-to-face, separated at one end by a 24 μm spacer, and not separated at the other end, to create a wedge-shaped optical cell. 5CB is introduced into this optical cell by first warming the 5CB to its isotropic phase, and drawing it into the cell by capillary action. Upon cooling, the liquid crystal assumes the patterned structures depicted in FIG. 6D.

Sample preparation. First, the inventors prepared two obliquely deposited gold films with deposition angle θi (shown in FIG. 6A, with the direction of gold deposition depicted as white arrow). Second, a polydimethylsiloxane (PDMS) elastomer was used to contact print defined regions of hexadecanethiol onto each substrate, shown in FIG. 6B. The entire substrate was then immersed into a 1 mM ethanolic solution of the EG4 thiol at room temperature for a pre-determined length of time, then rinsed with copious amounts of water and ethanol, and dried gently using a stream of nitrogen gas.

The orientations of nematic liquid crystal 5CB are sensitive to the molecular structure of the self-assembled monolayer (SAM) supported on the obliquely deposited gold film. 5CB will orient such that the easy axis, $\eta_0$ (depicted as black bar in FIG. 6C), on EG4 SAM is perpendicular to the direction of gold deposition. In contrast, 5CB will orient such that $\eta_0$ is parallel to the direction of gold deposition. Finally, the two SAMs are placed face-to-face, separated at one end by a 24 µm spacer, and not separated at the other end, to create a wedge-shaped optical cell. 5CB is introduced into this optical cell by first warming the 5CB to its isotropic phase, and drawing it into the cell by capillary action. Upon cooling, the liquid crystal assumes the patterned structures depicted in FIG. 6D). In Hybrid I and Hybrid II, the hybrid boundary conditions give rise to a uniform planar orientation of LC. For the Twisted LC in the absence of any torque, the twisted structure would be defined by the angular rotation of the easy axes $\eta_0$-bottom and $\eta_0$-top, defined as the angle δ in the manuscript.

Figure 7:
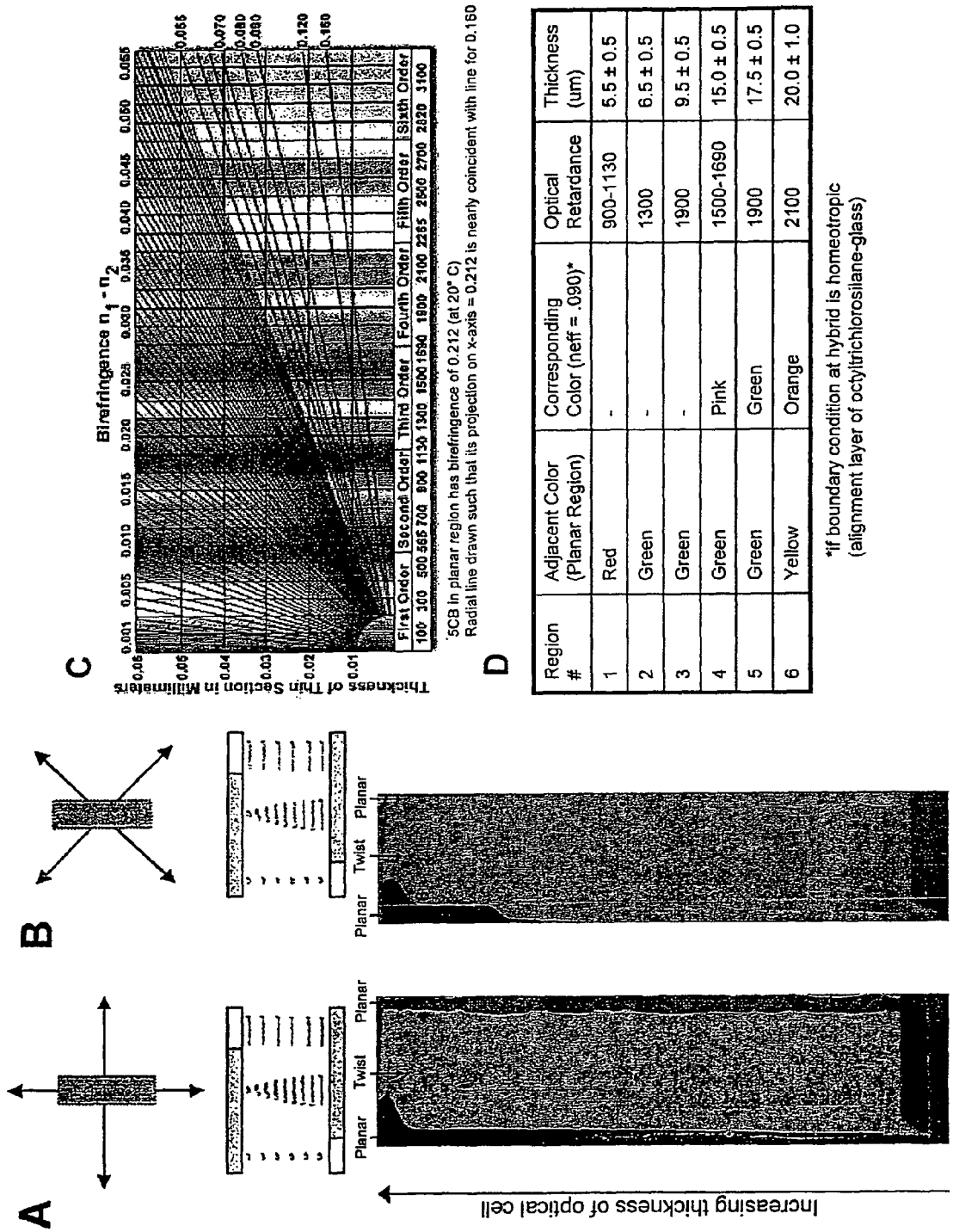
FIG. 7A illustrates a sample of liquid crystal positioned on the stage of a polarizing light microscope with source polarizer and analyzer set at 90°; B, ff both the analyzer and the polarizer are rotated 45°, it was observed that the Hybrid I/II regions modulate light, and appear as brightly colored interference bands; C, using the illustrated Michel-Levy interference chart, the observed interference color can be related to the thickness of the LC film, when the birefringence of the material is known; D, the optical appearance, measured optical retardance of the film, and estimated thicknesses for Regions 1-6 are depicted provided in this table.

Determination of cell thickness d at a given position in the sample. In this example, the inventors exploited the optical properties of the LC film in the Hybrid I/II regions to determine the cell thickness at a given position in the wedge-shaped optical cell. The sample of liquid crystal is positioned on the stage of a polarizing light microscope with source polarizer and analyzer set at 90° (FIG. 7A). Note that the region of twisted LC appears bright when viewed under crossed polarizers as it rotates plane polarized light. If the sample is positioned such that the orientation of the LC within Hybrid I/II is parallel to the source or analyzer, these regions are dark. If both the analyzer and the polarizer are rotated 45° (FIG. 7B), it was observed that the Hybrid I/II regions modulate light, and appear as brightly colored interference bands. The observed bands are caused by the wavelength-specific retardation of light passing through the film of liquid crystal as a function of thickness. Using the Michel-Levy interference chart (shown in FIG. 7C), the artisan can relate the observed interference color to the thickness of the LC film, when the birefringence of the material is known. The effective birefringence of 5CB in a uniform, planar orientation is equal to its known birefringence, or 0.212 (at 20° C., obtained from manufacturer).

Using the Michel-Levy chart, the behavior for a film of birefringence 0.212 was not described. To make use of the plot, the inventors drew a radial line extending from the origin at an angle such that its projection along the x-axis would result in the value 0.212. It was found that a line drawn this way was nearly co-incident with the line already drawn for a birefringence of 0.160.

To determine the thickness of the LC film for measurements taken at Regions 1-3 of the twisted nematic LC (denoted in white on FIG. 7B), the inventors noted the color of the interference band in the Hybrid I/II region immediately adjacent to the region of interest. In some samples, it is difficult to determine the order (first or second) of the color at the thinnest point of the sample. To find this, a quarter wave plate can be inserted into the path of light between the sample and the analyzer. The resultant shift in interference colors can be used to locate first order orange/red (observed at thin edge of Hybrid I, FIG. 7B). The optical behavior of a film with the birefringence of 0.212 is only useful for determining film thicknesses of 2-10 µm. Films of greater thickness can be accurately determined by examining the optical appearance of 5CB confined by a different hybrid boundary condition obtained via contact printing of octyltrichlorosilane onto glass. The effective birefringence of 5CB=0.090. The thicknesses of LC at Regions 4-6 can be estimated by noting the observed color in this patterned region. The optical appearance, measured optical retardance of the film, and estimated thicknesses for Regions 1-6 are depicted in FIG. 7D.

Optical determination of δ (relative orientation of $\eta_0$-bottom and $\eta_0$-top). Upon assembling the bottom and top surfaces into the wedge-shaped optical cell, it was common that the angle formed between $\eta_0$-bottom and $\eta_0$-top is not exactly 90°. Here, the inventors again make use of the patterned optical structures of LC when confined by the Hybrid I/II regions. To unambiguously determine the orientation of $\eta_0$-bottom, Hybrid II was viewed under polarized light microscopy (depicted in FIG. 8A). The inventors first rotated the sample on the stage such that the sample appears darkest when the source is set at 0°. This corresponds to a sample alignment such that $\eta_0$-bottom is exactly parallel to the source polarizer.

Next, the sample in Hybrid I was viewed. The orientations of the LC near the top and bottom of the film are depicted with respect to the source polarizer, shown in FIG. 8B. The orientation near the bottom is exactly 90° oriented from the $\eta_0$-bottom. Conversely, the orientation of the LC near the top is exactly parallel to $\eta_0$-top. The orientation of the director as one moves from bottom to top rotates at a small angle α (shown in FIG. 8B).

Figure 8:
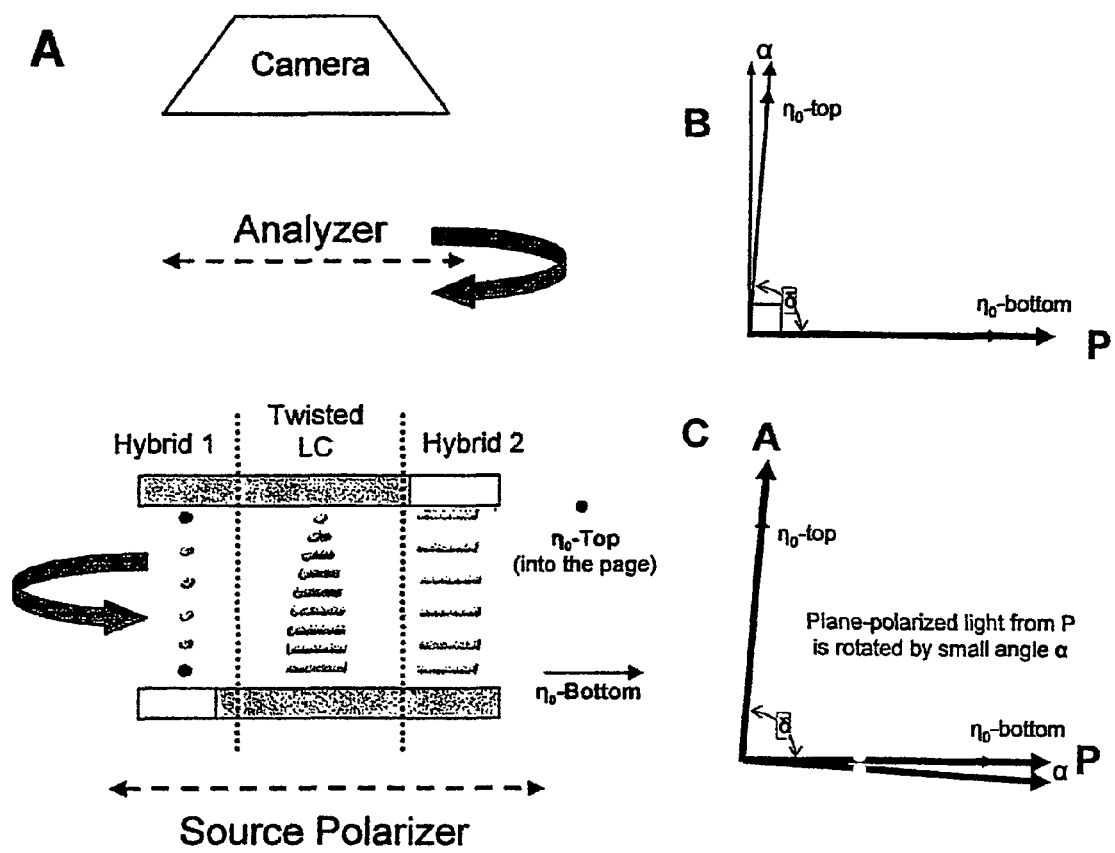
FIGS. 8A-C depict the determination of sample geometry δ.

Plane polarized light from the source is rotated by the small angle α as it passes through the LC film in Hybrid I, as shown in FIG. 8C. A minimum of transmitted light is observed if the analyzer polarizer (A) is at a position that is orthogonal to the plane polarized light exiting the film. The relative angle formed between the analyzer (A) and polarizer (P) when the minimum of transmitted light is observed is equal to δ.

Figure 9:
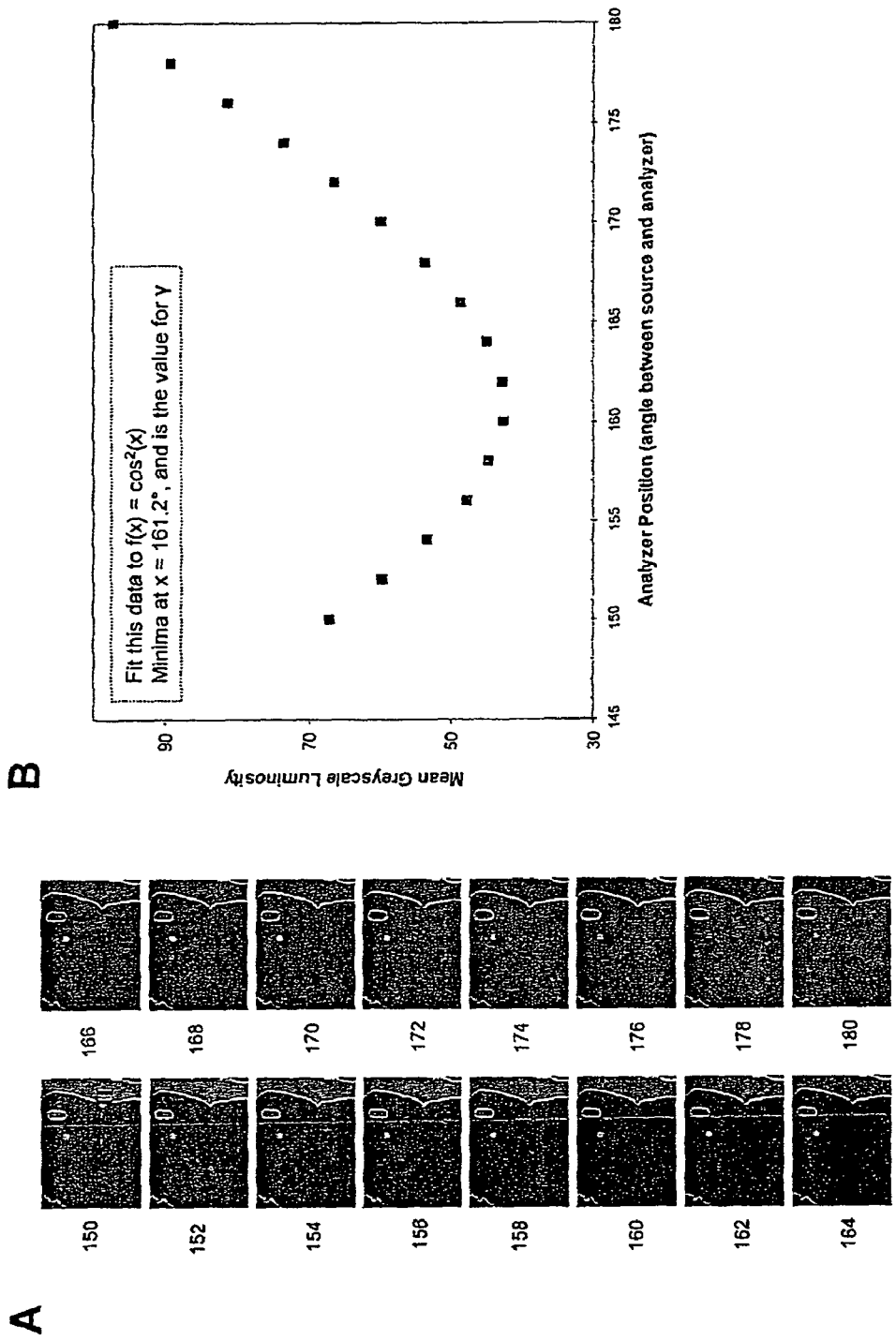
FIG. 9A shows optical images of twisted LC film at regularly spaced intervals of analyzer position; B, mean luminosity of domain I plotted as function of analyzer position.

Determination of $\Psi$ and $\phi$ for film of LC of known thickness. The inventors utilized the optical method described by Fonseca and Galerne, cited above. The sample is held at the fixed position on the microscope stage described in Part III. Next, the analyzer is rotated to a position such that a minima of transmitted light is observed. The relative angle formed between the analyzer and source polarizer is equal to $\gamma$. To determine $\gamma$, the inventors captured optical images of the twisted LC film at regularly spaced intervals of analyzer position, shown in FIG. 9A. Image processing (Adobe Photoshop) was used to determine the mean luminosity of the twisted domain of LC. For clarity, the mean luminosity of domain I was plotted as a function of analyzer position, shown in FIG. 9B. The magnitude of transmitted light, according to the optical behavior of twisted LCs in the waveguide region, can be fit to the function $f(x)=\cos^2(x)$. The inventors then fit the data set obtained to this function in order to obtain a more accurate measure of $\gamma$.

Figure 10:
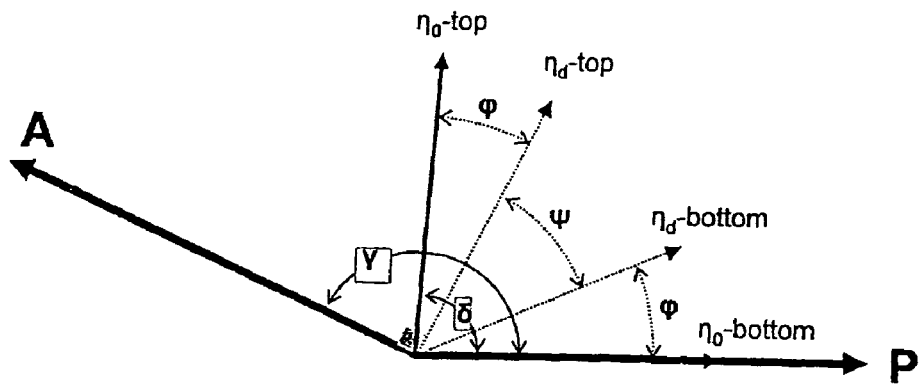
FIG. 10 depicts the angle diagram used to identify $\Psi$ and $\phi$ from the experimentally measured parameters δ and γ.

The angle diagram used by Fonseca to identify $\Psi$ and $\phi$ from the experimentally measured parameters $\delta$ and $\gamma$ is shown in FIG. 10. As the sample of twisted nematic LC is contained between two identically-treated surfaces, symmetry dictates that the director $\eta_d$ at both top and bottom will deviate at an angle $\phi$ from the easy axis. The angle $\gamma$, measured experimentally, is exactly orthogonal the equilibrium position of the director $\eta_d$-top. Therefore the angle formed between the source polarizer P and $\eta_d$-top is $(\gamma-90°)$ From Part 3 of this method, the inventors experimentally determined $\delta$; therefore $\phi=\delta-(\gamma-90°)$ can be calculated. This calculated value of $\phi$ can be used to determine the amount of twist $\Psi$ in the LC, as $\Psi$ is geometrically defined as $\Psi=\delta-2\phi$.

Example II

Liquid Crystals in Twisted Geometries for the Sensitive Detection of Changes in Interfacial Structure Caused by the Immobilization of Biomolecules Liquid crystals are fluids that possess orientational order over length scales that are large (μm) relative to the size of their molecular components (Å). When in contact with substrates having in-plane anisotropy, LCs can assume preferred orientation (defined as the easy axis $\eta_0$) over macroscopic distances. The control of the orientations by surfaces is described as anchoring. A variety of surface preparations including: rubbed polymer films, exposure of photoactive films to polarized radiation, and the oblique deposition of metals and metal oxides lead to macroscopic control over the orientation of LCs, by long-range and short-range forces.

Figure 11:
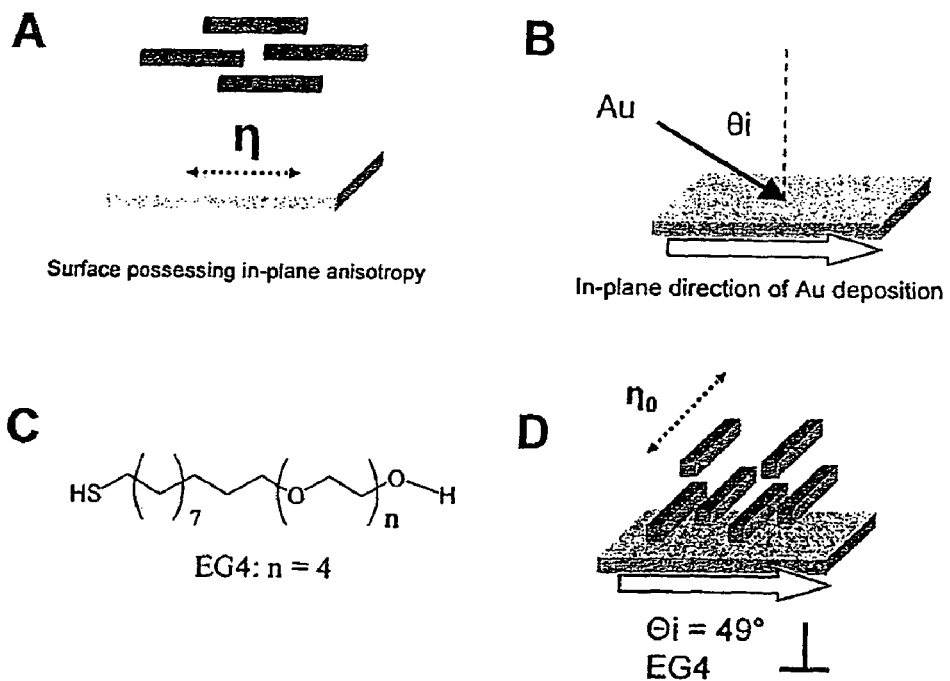
FIGS. 11A-D illustrate the preparation of substrates by the vapor deposition of thin gold films at an oblique (grazing) angle of incidence. These gold films are known to have in-plane anisotropic topography, and can be used to support self-assembled monolayers (SAMs).

The approach described in this example includes the preparation of substrates by the vapor deposition of thin gold films at an oblique (grazing) angle of incidence. These gold films are known to have in-plane anisotropic topography, and can be used to support self-assembled monolayers (SAMs) (see FIG. 11). By appropriate choice of thiol, the artisan can control the in-plane orientation of $\eta_0$. In addition, it is possible to manipulate how strongly the LC prefers that orientation—that is how much energy is required to perturb the LC away from $\eta_0$. This is defined as azimuthal anchoring energy, or W. In the previous example, the inventors measured this property for surfaces comprised of oligo(ethylene glycol)-terminated SAMs and demonstrated that the gold film morphology and monolayer structure can be used to manipulate this quantity.

The inventors have demonstrated that LCs can be used to amplify and report a wide range of interfacial phenomena occurring at these chemically-modified nano-structured interfaces including: chemical adsorption and transformations, and changes in interfacial structure caused by the binding/immobilization of peptides, proteins and viruses. In the context of previous studies using LCs to report the presence of bound peptide or protein at an interface, they have demonstrated that the presence of a thresh-hold amount of analyte at the interface leads to orientational changes of the LC at that interface. The difference in optical textures between uniformly oriented LC (no protein) and non-uniformly oriented LC (bound protein) serves as an easily interpreted optical signal.

Figure 12:
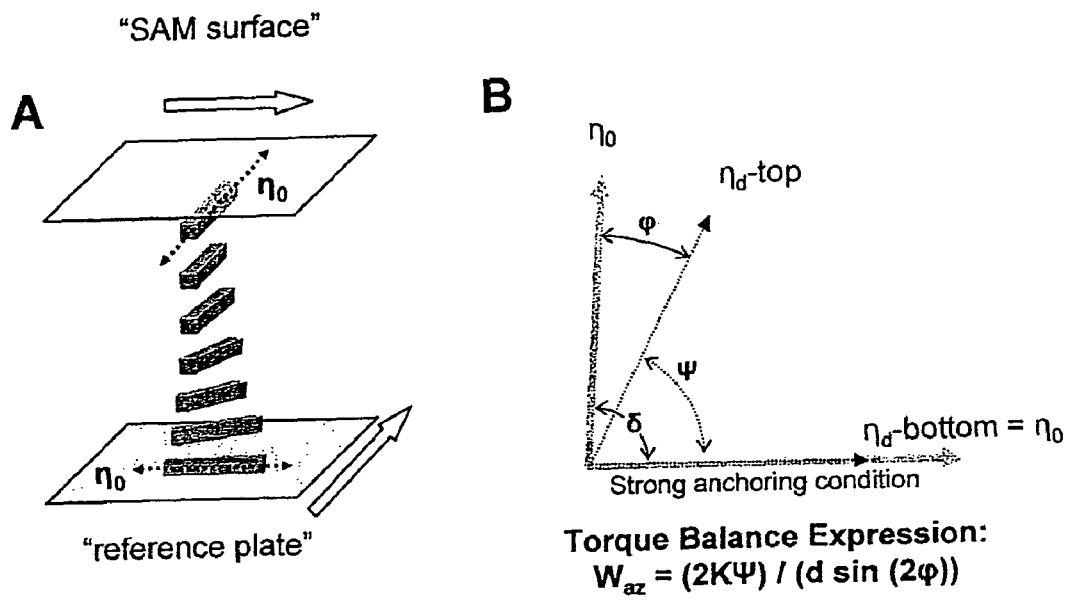
FIG. 12A depicts LCs confined between two surfaces such that $\eta_0$ at the top surface is rotated approximately 90° relative to the orientation of $\eta_0$ at the bottom surface. This induces a twist distortion across the LC film. For films that are sufficiently thin, the elastic bulk torque of the strained LC competes with the surface anchoring, and the equilibrium position of the director $\eta_d$ deviates at an angle $\phi$ from the easy axis; B, the angle diagram for the LC when confined between a surface of interest and a reference plate (having strong anchoring).

The inventors have used the elastic torque balance method to quantify azimuthal anchoring energies of LC in contact with EGX SAMs. To accomplish this, LCs are confined between two surfaces such that $\eta_0$ at the top surface is rotated approximately 90° relative to the orientation of $\eta_0$ at the bottom surface. This induces a twist distortion across the LC film, as depicted in FIG. 12A. For films that are sufficiently thin, the elastic bulk torque of the strained LC competes with the surface anchoring, and the equilibrium position of the director $\eta_d$ deviates at an angle $\phi$ from the easy axis. The angle diagram for the LC when confined between a surface of interest and a reference plate (having strong anchoring) is shown in FIG. 12B. The azimuthal anchoring energy, or Waz= $(2K\Psi)/(d \sin 2\phi)$. In this example, the methodology is described to demonstrate how increasing surface coverage of both peptides and proteins leads to changes in azimuthal anchoring energy. This method takes advantage of the ease of creating patterned SAMs, so as to be able to study multiple SAMs on one substrate and minimize the volumes of protein/peptide analyte solutions required to functionalize each surface of interest. This example further demonstrate that the present invention can consistently and accurately measure W for a substrate of known approximate anchoring energy. In addition, this example illustrates how the invention provides means for quantifying how W changes as both peptide and protein are systematically introduced to the interface.

Materials and Methods

Materials. All materials were used as received unless otherwise noted. Fisher's Finest glass slides were obtained from Fisher Scientific (Pittsburgh, Pa.). Gold 99.999% purity was obtained from International Advanced Materials (Spring Valley, N.Y.). Titanium 99.99% purity was obtained from PureTech (Brewster, N.Y.). Liquid crystal 4-cyano-4'-pentylbiphenyl (5CB) was obtained from EM Industries (New York, N.Y.) sold under the trademark name Licristal® (K15). Oligo (ethylene glycol)-terminated thiols were synthesized using previously published methods. The amine-terminated thiol (EG3-N) was obtained from Prochimia (Poland). Ethanol (200-proof) was obtained from Aaper Alcohol (Shelbyville, Ky.) and purged at least 1 hour with argon gas prior to use. Polydimethylsiloxane (PDMS) elastomeric stamps were prepared using Sylgard® 184 silicone elastomer kit obtained from Dow Corning (Midland, Mich.). Peptides IYGEFKKKC and I(pY)GEFKKKC were synthesized at the University of Wisconsin Biotechnology Center and purified by HPLC to yield products with >95% purity. Monoclonal anti-phosphotyrosine IgG was obtained from Sigma-Aldrich. Triethanolamine was obtained in 99% purity from Fisher. Phosphate buffered saline (PBS) was obtained from Sigma-Aldrich.

Preparation of Gold Substrates. Glass Slides were First Cleaned Using a Piranha solution as outlined in a prior publication. The slides were then positioned within the chamber of an electron beam evaporator such that the incidence angle of metal vapor flux to the substrate (defined with respect to the surface normal) could be controlled. The incident angles were measured manually using a digital level, with an accuracy of ±2°. All metal films were deposited at chamber pressures <1×10-6 torr and at deposition rates of <0.2 Å/s. First, a thin film of titanium (total thickness of 42-60 Å) was deposited onto the glass substrate to serve as an adhesion layer. Next, semi-transparent films of gold (total thickness 105-140 Å) were deposited onto the substrate. These substrates will be referred to as "obliquely deposited gold films". All gold substrates were used within 1 hour of removal from the evaporator chamber.

Figure 13:
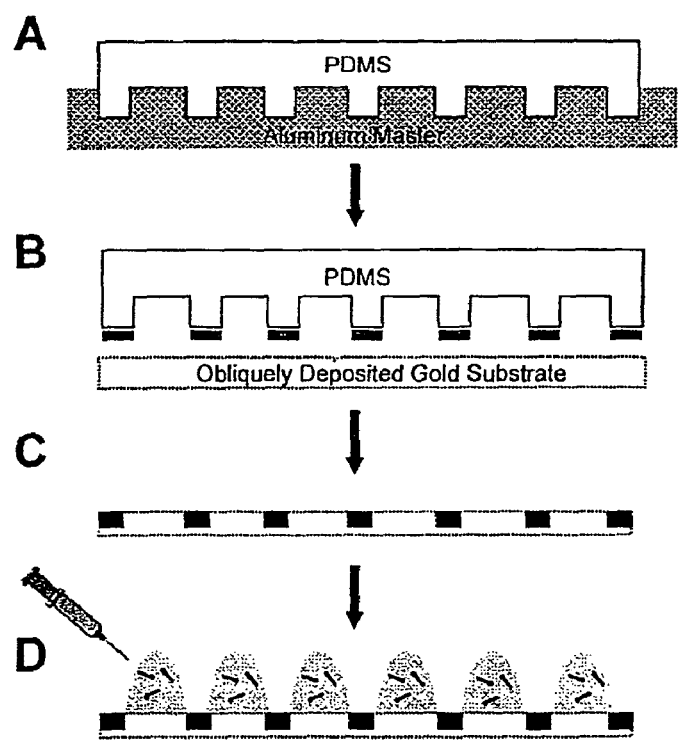
FIGS. 13A-D illustrates a procedure used to create patterned SAMs on gold substrate using a polydimethylsiloxane (PDMS) elastomeric stamp inked with 1 mM ethanolic solution of hexadecanethiol.

Formation of patterned self-assembled monolayers (SAMs). The procedure to create patterned self-assembled monolayers is outlined in FIG. 13. First, a polydimethylsiloxane (PDMS) elastomeric stamp with feature widths of 2-3 mm pitch and 2-3 mm height was cast from an aluminum master. The stamp was inked with a 1 mM ethanolic solution of hexadecanethiol, then gently dried using a stream of nitrogen gas. The stamp was placed in conformal contact with the obliquely deposited gold film for 5-10 seconds. Next, 1 mM solutions of oligo(ethylene glycol)-terminated thiols were prepared using argon purged ethanol. These solutions were stored under an argon atmosphere to prevent oxidation of the sulfhydryl functionality. Droplets of thiol solutions were applied to the gold substrate, confined between the patterned stripes of hexadecanethiol SAMs. The substrates were stored in a chamber saturated with ethanol vapor (to prevent droplet evaporation) for 18 hours, and then rinsed with copious amounts of water and ethanol, and then gently dried under a stream of nitrogen gas prior to placing them in contact with 5CB.

Preparation of Peptide-Modified Sams. the Chemistry Used to Attach Peptides to oligo(ethylene glycol)-containing SAMs is now described. In brief, 1 mM ethanolic solutions of thiols EG3-N and EG4 (where the mole fraction of amine-terminated component can vary) were arrayed onto patterned gold substrates using the above method. After the 18 hour SAM formation, surfaces were rinsed with copious amounts of ethanol and water and gently dried under an $N_2$ stream. Next, a 2 mM solution of the linker sulfo-SMCC (in 0.1 M triethanolamine buffer, pH 7.0) was applied as droplets to the monolayers for 30 minutes. These surfaces were rinsed briefly in water and dried. Next, 250 uM solution of a cysteine-terminated peptide (also in 0.1 M triethanolamine buffer, pH 7.0) was applied as droplets to the surface. The substrates were stored in a chamber saturated with water-vapor (to prevent droplet evaporation) for 3 hours. These surfaces were rinsed 3×5 mL 0.1 M triethanolamine buffer×5 minutes in and dried prior to use.

Protein Binding. Patterned arrays comprised of the peptide I(pY)GEFKKKC grafted onto SAMs formed only from 1:99 EG3N/EG4 were prepared as described above. Next, serial dilution was performed to prepare solutions of the protein anti-phosphotyrosine IgG in phosphate buffered saline with 0.05% triton-X (PBS+TX). The final protein concentrations were 180, 60, 18, 6, 1.8, 0.6, 0.18, 0 (PBS+TX) and 0 (PBS only). Each of these solutions was applied to a different region on the gold substrate as droplets, where the hexadecanethiol SAM served to confine each droplet. The substrate was stored in a chamber saturated with water vapor (to prevent droplet evaporation) for 2 hours. Next, the substrate was rinsed 1×45 seconds in PBS+TX and then 1×45 seconds in $H_2O$. The surface was gently dried under an $N_2$ stream prior to placing in contact with the liquid crystal.

Ellipsometry. A Rudolf-EL II ellipsometer (633 nm light @ 70° grazing angle of incidence) was used to determine the optical thickness of SAMs formed on reflective gold substrates (2000 Å gold/100 Å titanium adhesion layer prepared with θi=0.3-5 measurements were recorded for each sample. To estimate the thickness of the chemisorbed material, we used a 2-slab model assuming that the monolayer film supported on the gold substrate had a refractive index of 1.45.

Preparation of Optical Cell Having Wedge-Shaped Geometry. First, a Reference plate (assumed to have strong anchoring) was prepared by immersing an obliquely deposited gold substrate (θi=62°) in a 1 mM solution of pentadecanethiol for 2 hours, then rinsing with copious amounts of ethanol and water before drying. The patterned SAM of interest was placed face-to-face against this reference plate, such that in-plane direction of gold deposition of the reference plate was rotated approximately 90° relative to the in-plane direction of gold deposition of the top surface (Shown in FIG. 14A). The surfaces were separated by a 12 μm spacer at one end, and were not separated by a spacer at the other end, to create a wedge-shaped cell (Shown in FIG. 14B). The optical cell, and 5CB, were both warmed to approximately 40-45° C. (above the clearing point for 5CB). 5CB was then drawn into the optical cell by capillary action and slowly cooled to room temperature. Measurements of the optical properties of the LC film for all samples were taken after 30 minutes of cooling to room temperature (22° C.), as both temperature and age of the sample (surface gliding) are known to influence the measured anchoring strength.

Optical determination of d, δ, Ψ and φ. Measurements were taken using a polarized light microscope (BX 60, Olympus) equipped with an X-Y translating stage and fitted with a digital camera for image capture. The optical method used to determine the thickness and the equilibrium position of the director is described above which was adapted from methods published by Fonseca and Galerne.

Results and Discussion

Part 1. Anchoring Energy for EG4 SAM Spatially-arrayed onto Gold Substrate

This section of the example describes a method according to the invention for measuring the azimuthal anchoring energy for SAMs that are spatially-arrayed onto a single substrate. Using patterned arrays has the advantage of requiring smaller volumes of solutions needed to prepare the substrate. This also permits multiple measurements on one substrate. In studying patterned arrays, the example will be confined to the liquid crystal between the array and a reference plate (See, e.g., the structure illustrated in FIG. 12A). If the present method is to have utility in the study of biomolecular interactions occurring at surfaces, it first needs to be demonstrated that it yields consistent measurements of W and that assumptions regarding the reference plate (strong anchoring conditions) are correct and lead to an accurate measure of W.

Figure 14:
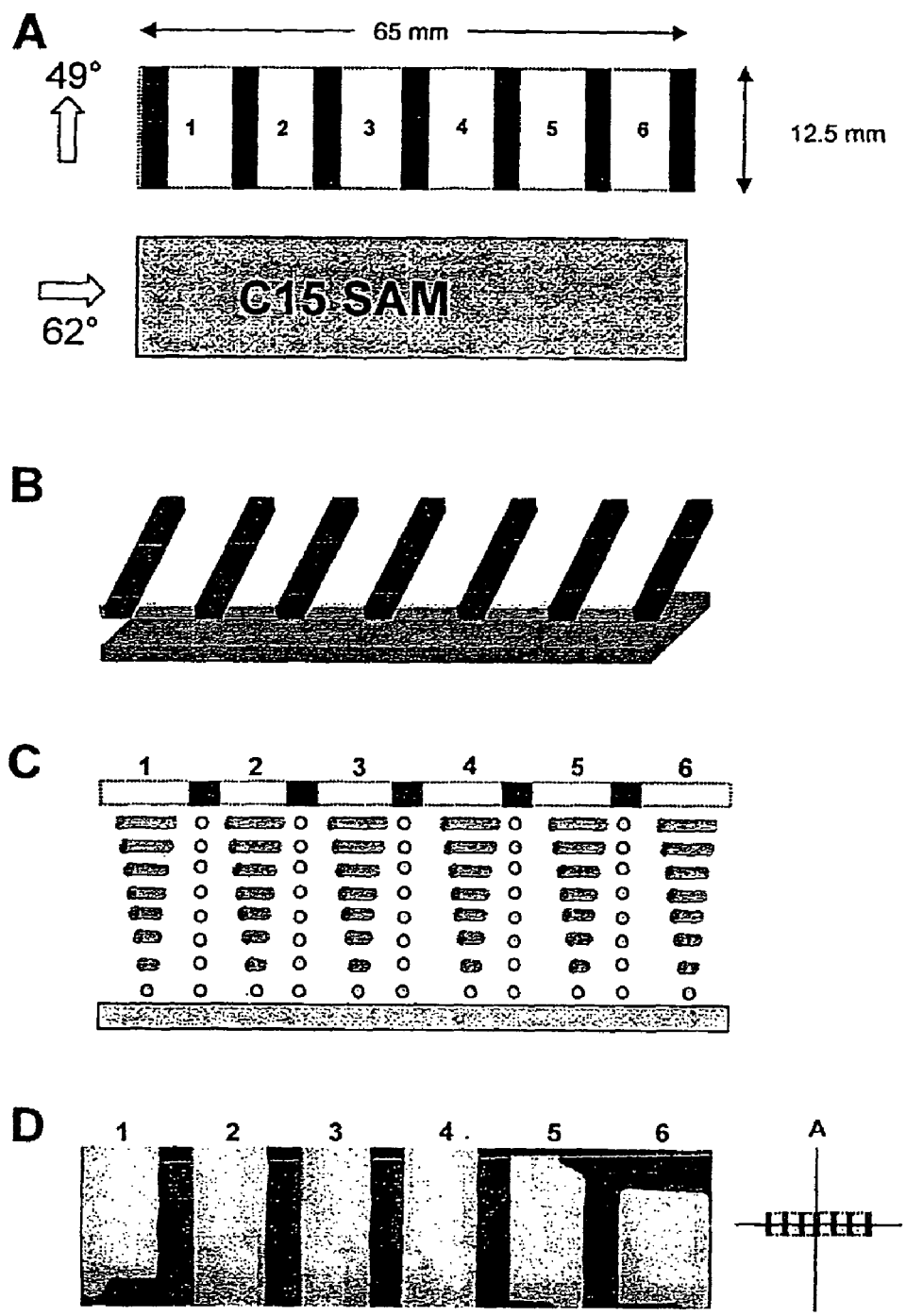
FIG. 14A illustrates an array of EG4 SAMs which were separated by contact-printed regions of hexadecanethiol SAMs supported on an obliquely deposited gold substrate; B, the two surfaces were assembled into a wedge-shaped optical cell. The LC and optical cell were warmed to 40-45° C. (above the clearing point of 5CB), and the LC was drawn into the optical cell by capillary action. The sample was cooled to room temperature and viewed using polarized light microscopy; C, upon cooling, the patterned boundary conditions give rise to patterned structures in the bulk liquid crystal; D, when viewed under polarized light microscopy when the polarizer and analyzer are set at 90°, the patterned LC structures are visually apparent. Regions 1-6 of the sample appear bright, as plane-polarized light from the source is rotated as it passes through the twisted LC.

First, an array of EG4 SAMs was prepared which were separated by contact-printed regions of hexadecanethiol SAMs supported on an obliquely deposited gold substrate (depicted in FIG. 14A). The reference plate is a pentadecanethiol SAM supported on a gold film deposited at a large oblique angle of incidence (θi=62°). This large angle was expected give rise to a strong anchoring boundary condition. Next, the two surfaces were assembled into a wedge-shaped optical cell (FIG. 14B). The LC and optical cell were warmed to 40-45° C. (above the clearing point of 5CB), and the LC was drawn into the optical cell by capillary action. The sample was cooled to room temperature and viewed using polarized light microscopy.

Upon cooling, the patterned boundary conditions give rise to patterned structures in the bulk liquid crystal (shown in FIG. 14C). The LC orients such that $\eta_o$ is perpendicular to the direction of gold deposition for both EG4 and pentadecanethiol SAMs. As the two substrates are assembled such that the gold deposition directions are rotated, this induces a twisted deformation in the LC. In contrast, the orientation of LC at the hexadecanethiol pattern at the top surface is parallel to the direction of gold deposition. This boundary condition leads to a uniformly planar orientation in the bulk LC. When viewed under polarized light microcopy when the polarizer and analyzer are set at 90°, the patterned LC structures are visually apparent. Regions 1-6 of the sample appear bright, as plane-polarized light from the source is rotated as it passes through the twisted LC (see FIG. 14D). In contrast, the non-twisted LC structures appear dark, as the polarization of light undergoes little rotation and thus light is not transmitted through the analyzer.

Figure 15:
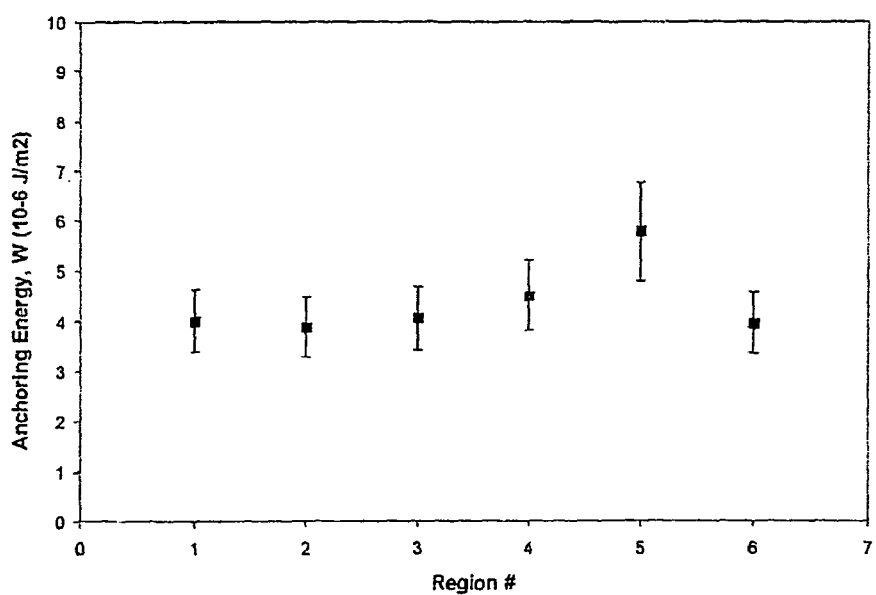
FIG. 15A provides a table of the azimuthal anchoring energy W measured at each EG4 SAM interface by finding the equilibrium position of the director for the LC film of thickness d=5.5±0.5 μm. This could be used to estimate the angle of deviation from the easy axis of the top surface (defined as $\phi$) and the amount of twist in the LC ($\Psi$). Using the torque balance expression, we calculate W using the measured $\phi$ and $\Psi$. The anchoring energy for each interface is summarized in the table, and depicted visually in FIG. 15B.

The azimuthal anchoring energy W was then measured at each EG4 SAM interface by finding the equilibrium position of the director for the LC film of thickness d=5.5±0.5 μm. This could be used to estimate the angle of deviation from the easy axis of the top surface (defined as $\phi$) and the amount of twist in the LC ($\Psi$). These values are summarized in FIG. 15A. Using the torque balance expression, W was calculated using the measured $\phi$ and $\Psi$. The anchoring energy for each interface is summarized in the table of FIG. 15A, and depicted visually in FIG. 15B.

The value W for EG4 SAMs was previously measured on obliquely-deposited gold films ($\theta i=41°$ and $\theta i=58°$) using symmetrically-constructed optical cells, and these were found to have W of 1.45±0.28 μJ/m2 and 5.76±0.69 μJ/m2, respectively. It was expected that EG4 supported on gold films prepared at an oblique angle that falls between these would have W that also falls between these two measurements. Accordingly, the measurements of W for EG4 SAMs arrayed onto $\theta i=49°$ consistently fall within this expected range. Therefore, the use of a reference plate to study W for patterned SAMs is consistent and accurate.

Part 2. Anchoring Energy for LC in Contact with Peptide-Modified SAMs

Figure 16:
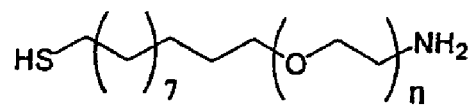
FIGS. 16A-C show the preparation of substrate with arrayed regions of peptide-modified SAMs.
Figure 16:
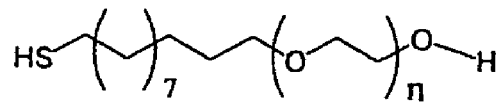
Figure 16:
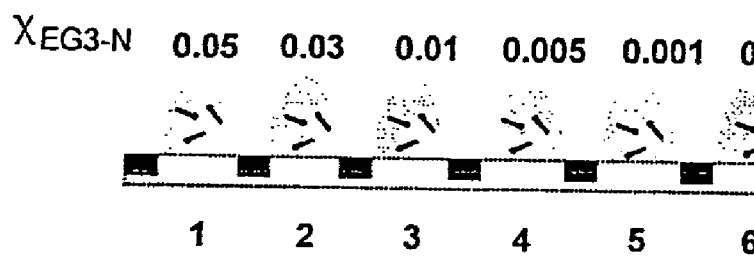
Figure 16:
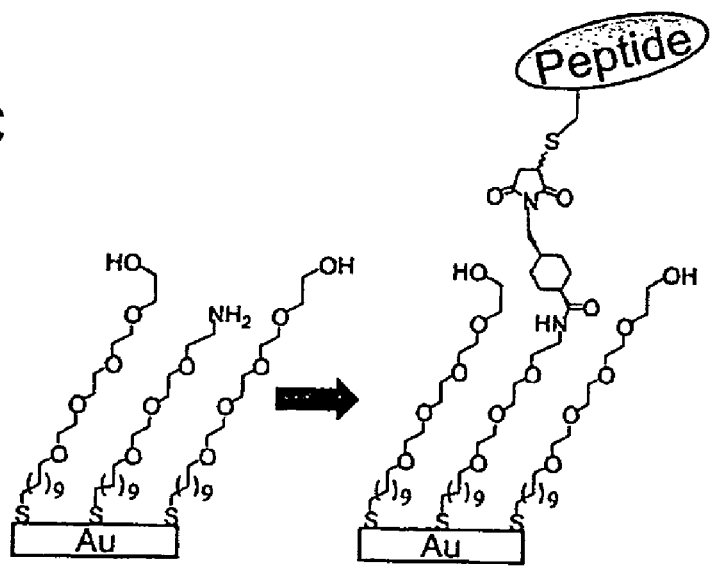

The above-described method was then applied to peptide-modified SAMs arrayed onto obliquely-deposited gold substrates ($\theta i=49°$). The inventors prepared arrays of two-component monolayers formed from thiols EG3-N and EG4, where they systematically increased the mole fraction of the amine component in the formed monolayer—from 0 to 0.05—and depicted in FIG. 16. Next, using previously published methods, the inventors grafted the peptide sequence IYGEFKKKC onto the two-component monolayer. In this way, surfaces that present controlled areal density of the immobilized peptide were created.

Figure 17:
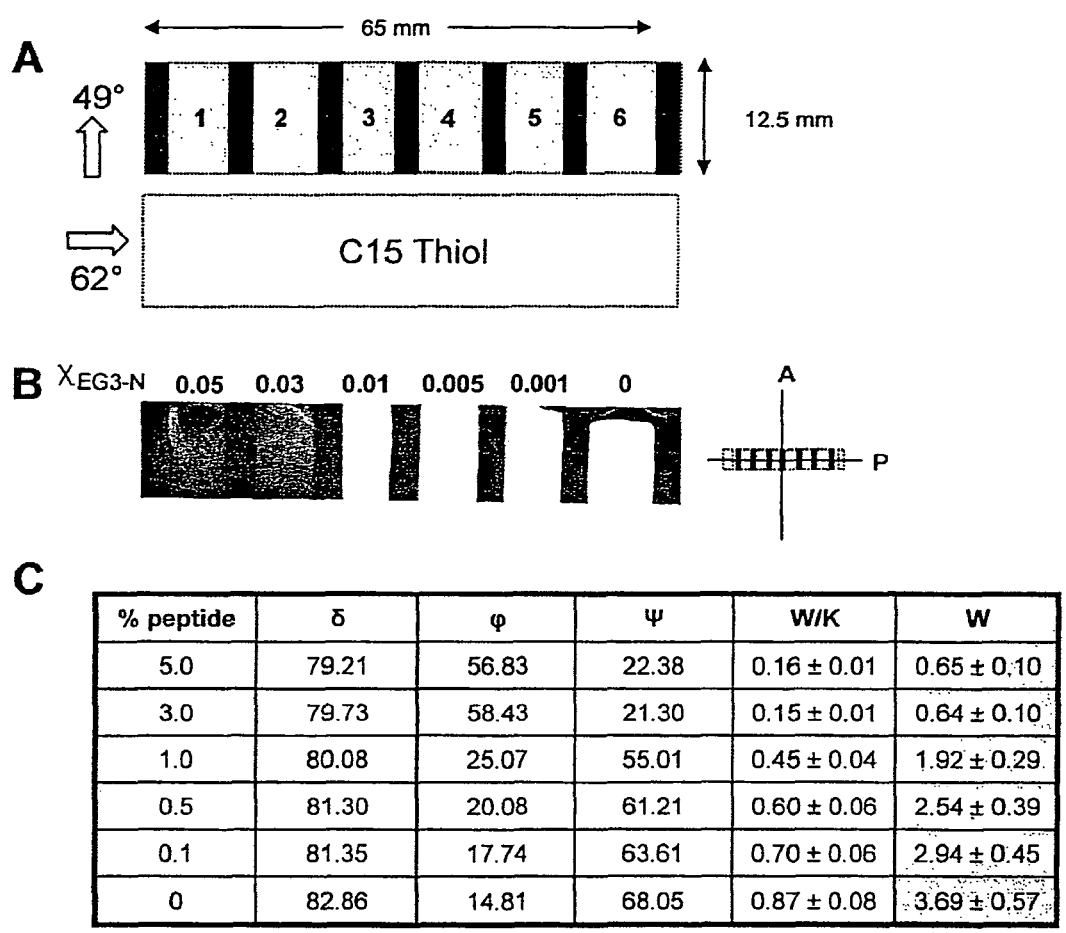
FIGS. 17A-C illustrate additional preparation and values related to substrates with arrayed regions of peptide-modified SAMs.

An optical cell was then assembled that comprised the peptide-modified substrate and a reference plate, shown in FIG. 17A. LC was introduced into the optical cell and the appearance of the sample was viewed under crossed polarized microscopy (shown in FIG. 17B). Beginning from the rightmost end of the sample, the LC is in contact with the EG4 SAM and the bright optical texture is very similar to what was observed for the EG4 array in Part 1 of this example. Moving from right to left, the LC in contact with surfaces 0.001, 0.005, 0.01 are also bright, indicating that a twisted LC structure has formed. However, the LC in contact with 0.03 and 0.05 is dark, indicating a loss of twist in the LC.

Figure 18:
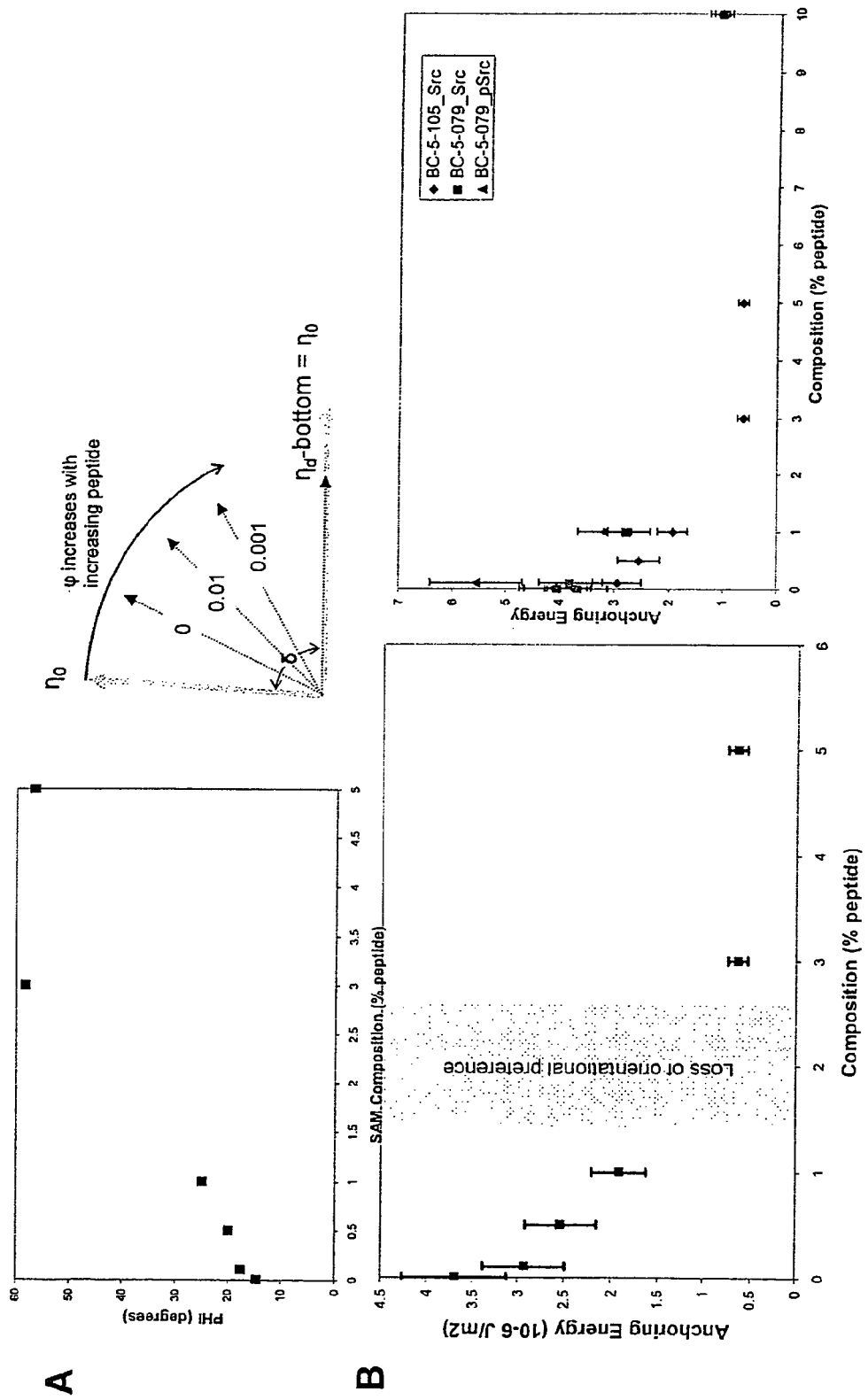
FIGS. 18A-B depict anchoring energy W on a substrate surface as a function of surface composition.

The optical method was then used to characterize the equilibrium position of the director at each interface, summarized in FIG. 17C. It was found that the measurement of W for the surface with no peptide (EG4 SAM) falls within the expectations from the measurements in Part I. Next, it was found that the deviation of the director from the easy axis ($\phi$) increases with increasing surface coverage of the immobilized peptide, depicted in FIG. 18A. If W was plotted as a function of surface composition, it was observed that the anchoring energy of the substrate is systematically lowered with increasing surface coverage of the immobilized peptide.

These results demonstrate that increasing peptide surface coverage leads to systematic changes in the W of the interface. At a threshold surface coverage, a complete loss in orientational preference occurs at the interface leading to the observed dark textures of the LC. The liquid crystal, when confined in the strained, twisted geometry is more sensitive to changes in interfacial structure. That is, the inventors could detect measurable changes in LC behavior optically when in contact with surfaces presenting very low amounts of peptide. If it is assumed that the thiols in the SAM have an intermolecular spacing of 4.97 Å, and that the peptide is grafted at 100% efficiency (a high estimate of peptide coverage), it is then estimated that for a surface prepared at 0.005 mole fraction of EG3-N would present ~0.75 ng (750 pg) peptide/mm2. Artisans have previously calculated the sensitivity of peptide detection for OWLS (~100 ng) and SPR (~20 pg) and IR (~20 pg). Also, these low surface coverages are applicable in the context of cell behavior.

Figure 19:
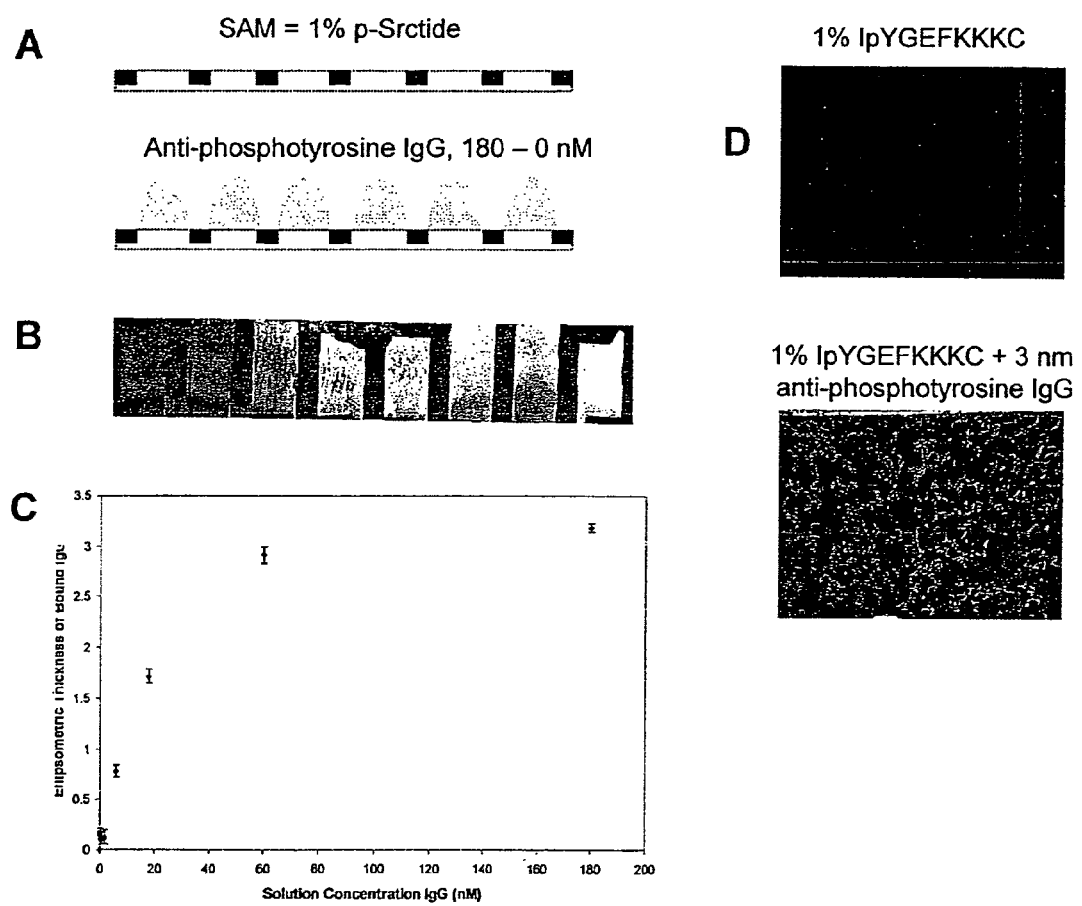
FIGS. 19A-D illustrate liquid crystal behavior in contact with surfaces presenting bound protein analyte.

Part 3. Anchoring Energy for LC in Contact with Surfaces Presenting Bound Protein In this part of the example, the methodology described above is used in determining changes in anchoring energy brought about by the systematic increase in bound protein analyte. The inventors prepared SAMs having identical composition (0.01 EG3-N) and grafted the peptide sequence IpYGEFKKKC to each SAM using the methods described in Part 2, as depicted in FIG. 19A. Serial dilution was then used to prepare solutions with varied concentration of the protein anti-phosphotyrosine IgG over the range of 0 to 180 nM. Each solution was applied as a droplet to different peptide-modified SAMs for two hours and then rinsed. These substrates were assembled into a wedge-shaped optical cell as done previously, using a reference plate formed from pentadecanethiol on oblique gold ($\theta i=62°$). The optical appearance of the LC when viewed under crossed polarized microscopy is shown in FIG. 19B. In addition, the amount of protein captured at the surface was monitored by recording changes in the optical thickness after the protein binding step. The optical thickness of the protein layer (as a function of the protein concentration in the droplet applied) after 2 hours of binding is depicted in FIG. 19C.

One will note the optical appearance of the LC when in contact with the patterned substrate illustrated in FIG. 19B. At the rightmost end of the sample, which corresponds to a peptide-modified SAM having no bound protein, exposed to only buffer, the LC appears bright due to the twisted LC structure. As one moves from right to left in FIG. 19B, the LC is bright, but when in contact with surfaces that present ~3 nm of bound protein, the LC is dark. The loss of twist leads to an optical texture that reports the presence of bound protein immediately after sample preparation, and is an improvement on our previously published approaches. In addition, if one compares the optical textures of LC when confined by two surfaces presenting 3 nm of bound protein, but arranged such that the gold deposition directions are aligned parallel, it is found that the presence of the protein is not reported in this system, depicted in FIG. 19D.

Figure 20:
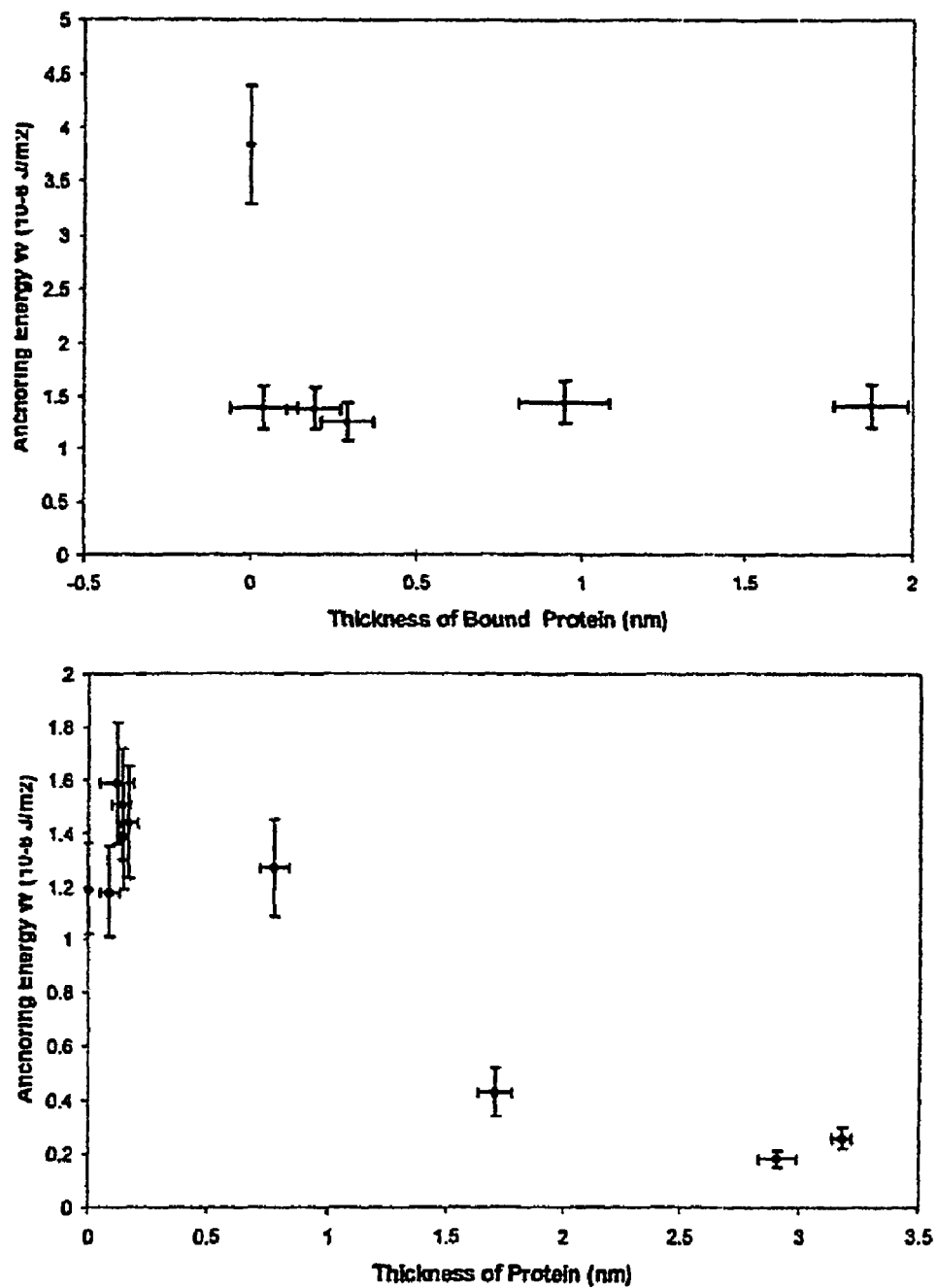
FIG. 20 depicts two plots of anchoring energy W versus thickness of increasing amounts of bound IgG.

The inventors further quantified changes in anchoring energy brought about by the systematic introduction of analyte to the interface. They were able to measure the equilibrium position of the director, and find $\delta$, $\phi$, $\Psi$ for LC films of thickness 7.0±0.5 µm for each region. These values were then used in calculations of W, as described previously. A plot of W vs. ellipsometric thickness of bound protein is shown for two different experiments in FIG. 20.

This example demonstrates that the increase of peptide and protein analytes at an interface results in systematically lowered azimuthal anchoring energies of a substrate. As these changes in W can be measured at analyte coverage lower than what is required to drive orientational changes, this provides the basis of a more sensitive method to detect biomolecular binding events using LCs. The inventors demonstrate the detection of immobilized peptide at ~750 pg (0.75 ng)/mm2 coverage, similar to that reported by SPR and OWLS and ATR-IR.

The following disclosure is provided to ensure thorough description of the methods described in this second example section. This information is organized into four parts: 1) sample preparation, 2) determination of cell thickness d, 3) determination of $\delta$ and 4) determination of $\Psi$ and $\phi$. For consistency, this method was used for the analysis of the anchoring energy of 5CB in contact with EG4 on oblique gold prepared using a deposition angle of $\theta i=58°$.

1. Sample assembly. Spatially-arrayed SAMs were prepared on gold films having been prepared by vapor deposition at $\theta i=49°$, as described above. An optical cell was fabricated using this substrate and a reference plate comprised of a pentadecanethiol SAM supported on a different obliquely deposited gold substrate ($\theta i=62°$) where the direction of gold deposition is indicated by the white arrow in FIGS. 21A-C.

Figure 21:
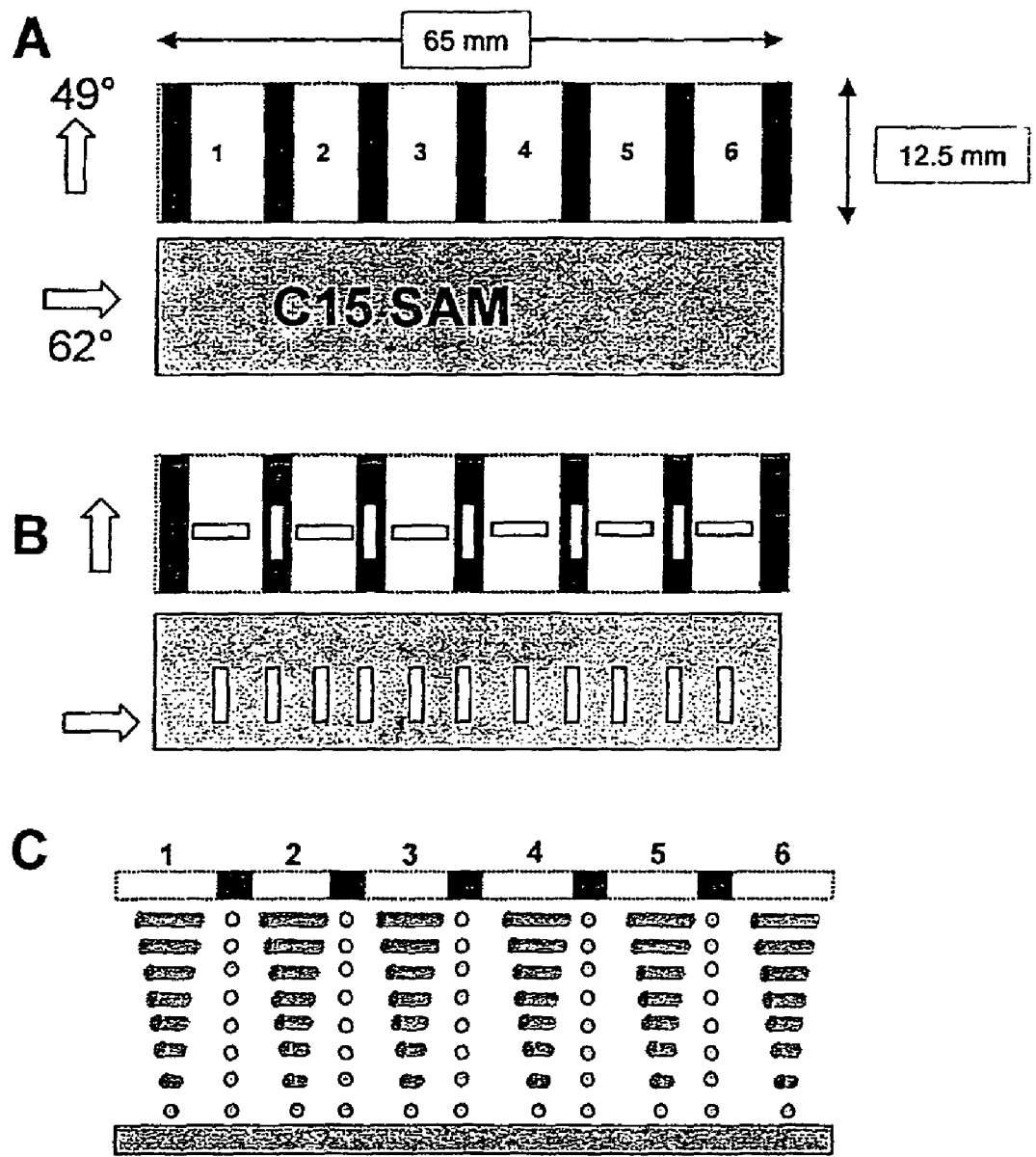
FIGS. 21A-C provide a schematic of an optical cell including a substrate and a reference plate comprised of a pentadecanethiol SAM supported on a different obliquely deposited gold substrate (θi=62°) where the direction of gold deposition is indicated by the white arrow.

The orientations of nematic liquid crystal 5CB are sensitive to the molecular structure of the self-assembled monolayer (SAM) supported on the obliquely deposited gold film. The orientations of the LC at the two confining surfaces are depicted in FIG. 21A. 5CB will orient such that the easy axis, $\eta_0$ (depicted as white bar in FIG. 21B), on EG4 SAM is perpendicular to the direction of gold deposition. In contrast, 5CB in contact with the contact printed hexadecanethiol SAM will orient such that $\eta_0$ is parallel to the direction of gold deposition. At the bottom surface, 5CB in contact with pentadecanethiol SAM will orient such that $\eta_0$ is perpendicular to the direction of gold deposition. Finally, the two SAMs are placed face-to-face, separated at one end by a 12 µm spacer, and not separated at the other end, to create a wedge-shaped optical cell (depicted in FIG. 14B). 5CB is introduced into this optical cell by first warming the 5CB to its isotropic phase, and drawing it into the cell by capillary action. Upon cooling, the liquid crystal assumes the patterned structures depicted in FIG. 21C. The hybrid boundary conditions of C15 and C16 give rise to a uniform planar orientation of LC. The angular rotation of the easy axes that result in twisted LC structures ($\eta_0$-bottom and $\eta_0$-top) is defined as the angle $\delta$ in the manuscript.

2. Determination of Cell Thickness d at a Given Position in the Sample

Figure 22:
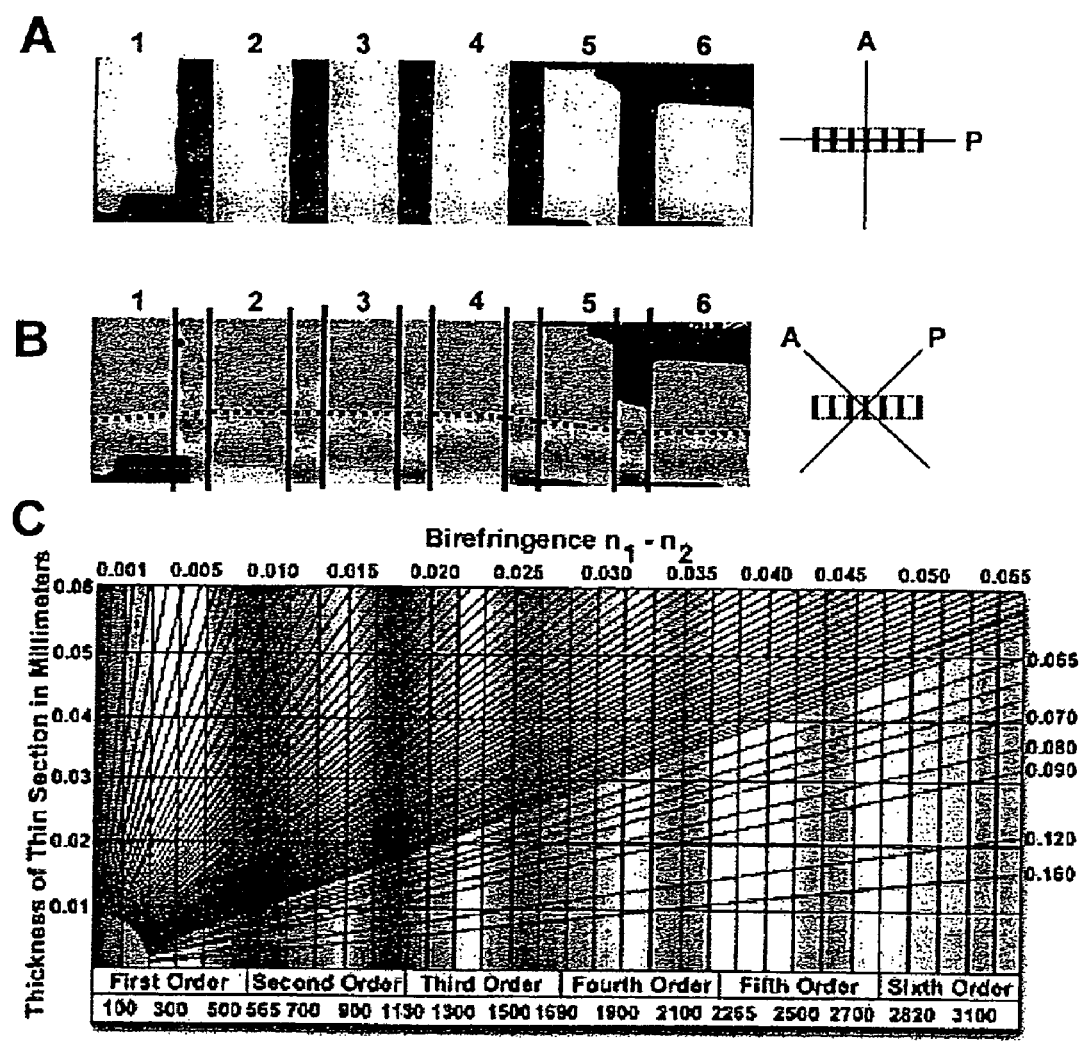
FIG. 22A depicts a sample of liquid crystal positioned on the stage of a polarizing light microscope with source polarizer and analyzer set at 90°; B, rotation of analyzer and the polarizer 45° yields hybrid regions modulating light, and appearing as brightly colored interference bands; C, the Michel-Levy interference chart referred to in Example 2.

The optical properties of the LC film in the hybrid regions are exploited in the present invention to determine the cell thickness at a given position in the wedge-shaped optical cell. The sample of liquid crystal is positioned on the stage of a polarizing light microscope with source polarizer and analyzer set at 90° (FIG. 22A). It is noted here that the region of twisted LC appears bright when viewed under crossed polarizers as it rotates plane polarized light. The optical appearance of the LC confined in the hybrid region is dark, when the orientation of the LC is parallel to either polarizer or analyzer.

If one rotates both the analyzer and the polarizer 45° (FIG. 22B), it is found that the hybrid regions modulate light, and appear as brightly colored interference bands. The observed bands are caused by the wavelength-specific retardation of light passing through the film of liquid crystal as a function of thickness. Using the Michel-Levy interference chart (shown in FIG. 22C), one can relate the observed interference color to the thickness of the LC film, when the birefringence of the material is known. The effective birefringence of 5CB in a uniform, planar orientation is equal to its known birefringence, or 0.212 (at 20° C., obtained from manufacturer).

Based on the Michel-Levy chart, the behavior for a film of birefringence 0.212 was not described. To make use of the plot, the inventors drew a radial line extending from the origin at an angle such that would intercept the x-axis at a value of 0.212. It was found that a line drawn this way was nearly co-incident with the line already drawn for a birefringence of 0.160.

To determine the thickness of the LC film for measurements taken at Regions 1-6 of the twisted nematic LC, it was noted the color of the interference band in the hybrid region immediately adjacent to the region of interest. In some samples, it is difficult to determine the order (first or second) of the color at the thinnest point of the sample. To find this, a quarter wave plate can be inserted into the path of light between the sample and the analyzer. The resultant shift in interference colors can be used to locate first order orange/red (observed at thin edge of Hybrid I, FIG. 22B). The optical behavior of a film with the birefringence of 0.212 is only useful for determining film thicknesses of 2-10 µm. In the example shown in FIG. 22B, all measurements were taken along the grey-dotted line, where the optical appearance of the LC in the hybrid region was blue, third order and having an optical retardance of ~1130. This corresponds to a thickness of 5.5±0.5 µm.

3. Optical Determination of $\delta$ (Relative Orientation of $\eta_0$-bottom and $\eta_0$-top)

Upon assembling the bottom and top surfaces into the wedge-shaped optical cell, it is very common that the angle formed between $\eta_0$-bottom and $\eta_0$-top is not exactly 90°. Here, the inventors made use of the patterned optical structures of LC when confined by hybrid boundary conditions. To unambiguously determine the orientation of $\eta_0$-bottom, the LC confined in the hybrid region was viewed under polarized light microscopy (depicted in FIG. 23A). The sample on the stage is first rotated such that the LC in the hybrid region appears darkest when the source is set at 0°. This corresponds to a sample alignment such that $\eta_0$-bottom is exactly parallel to the source polarizer.

Next, the orientation of LC at the top surface in the hybrid region was characterized. The orientations of the LC near the top and bottom of the film are depicted with respect to the source polarizer, shown in FIG. 23B. The orientation near the bottom is parallel to $\eta_0$-bottom. Conversely, the orientation of the LC near the top is rotated exactly 90° with respect to $\eta_0$-top. The orientation of the director as one moves from bottom to top rotates at a small angle $\alpha$ (shown in FIG. 23B).

Figure 23:
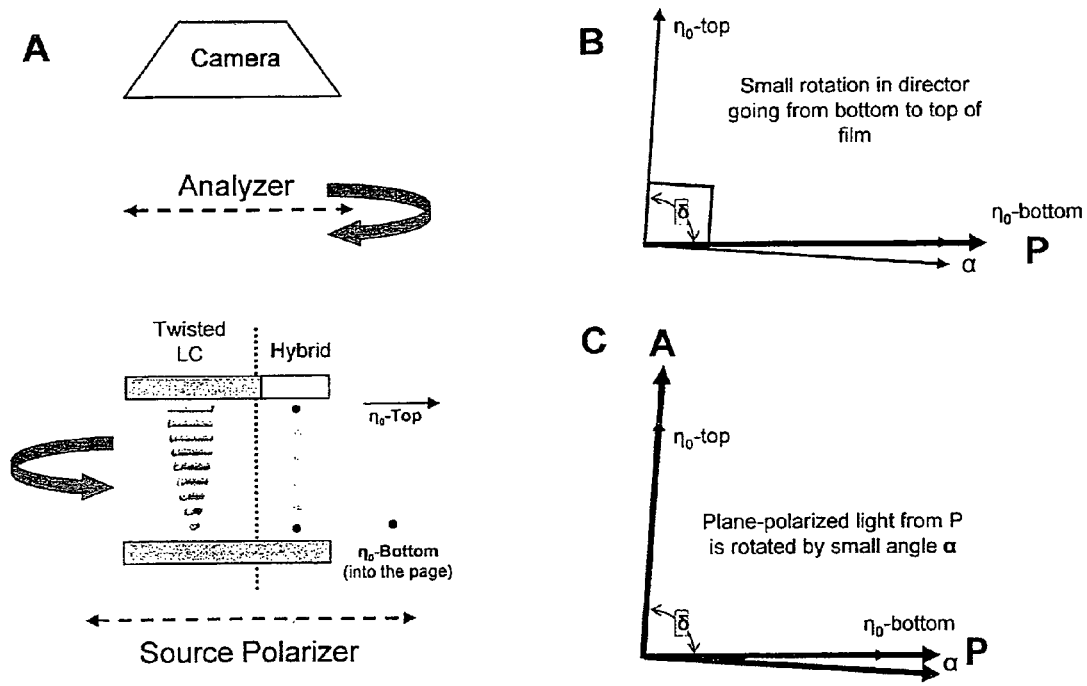
FIGS. 23A-C illustrate the optical determination of δ (relative orientation of $\eta_0$-bottom and $\eta_0$-top).

Plane polarized light from the source will be rotated by the small angle $\alpha$ as it passes through the LC film in the hybrid region, as shown in FIG. 23C. A minimum of transmitted light will be observed if the analyzer polarizer (A) is at a position that is orthogonal to the plane polarized light exiting the film. The relative angle formed between the analyzer (A) and polarizer (P) when the minimum of transmitted light is observed is equal to $\delta$.

4. Optical Determination of δ and γ to Estimate Ψ and φ for Film of LC of Known Thickness.

Figure 24:
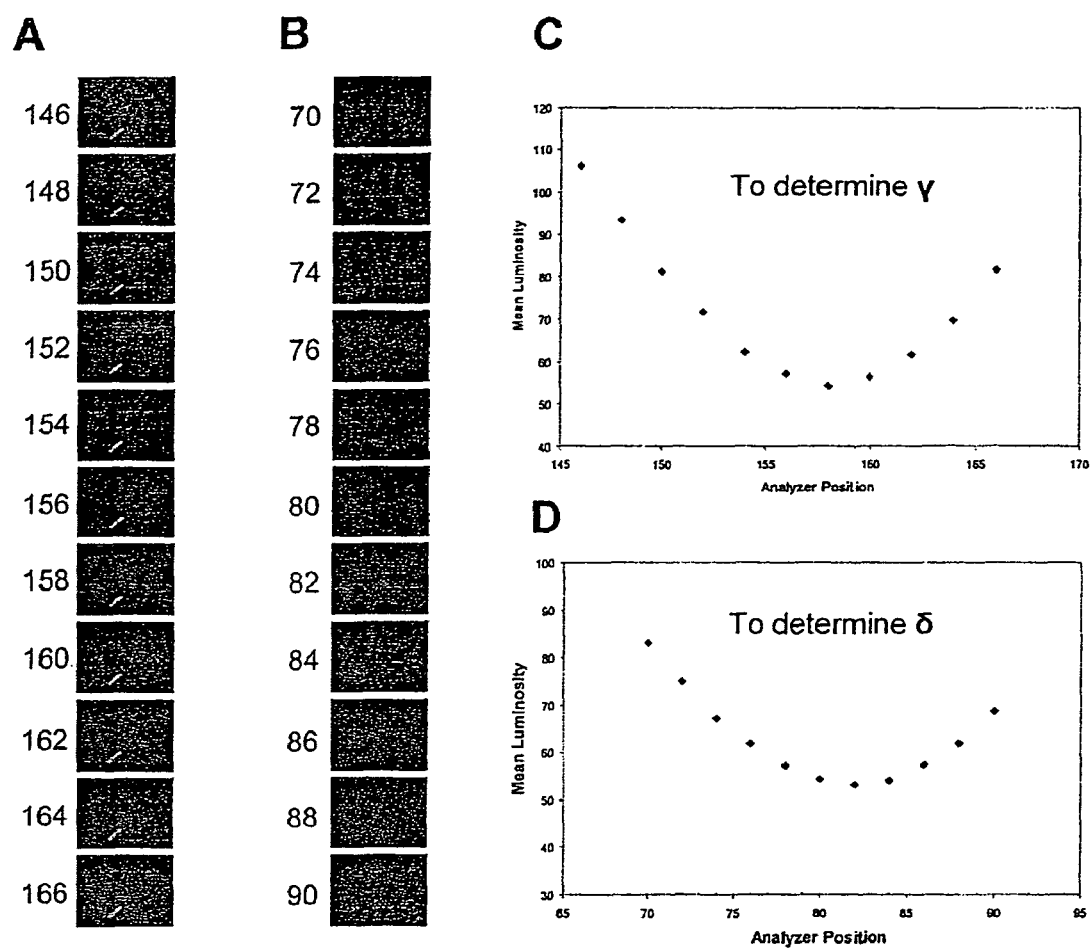
FIGS. 24A-D depict steps in the optical determination of δ and γ to estimate $\Psi$ and $\phi$ for a film of LC of known thickness.

As described above, this embodiment of the present invention uses an optical method to determine the equilibrium position of the director. The sample is held at the fixed position on the microscope stage described in Part III. Next, the analyzer is rotated to a position such that a minimum of transmitted light is observed. The relative angle formed between the analyzer and source polarizer is equal to γ. To determine γ, the inventors captured optical images of the twisted LC film at regularly spaced intervals of analyzer position, shown in FIG. 24A. Optical images as a function of analyzer position were also captured when viewing the hybrid region, shown in FIG. 24B. Image processing (Adobe Photoshop) was used to determine the mean luminosity of the twisted domain of LC. For clarity, the mean luminosity of domain I was plotted as a function of analyzer position, shown in FIG. 24C. The magnitude of transmitted light, according to the optical behavior of twisted LCs in the waveguide region, can be fit to the function $f(x)=\cos^2(x)$. The inventors fit the data set obtained to this function in order to obtain a more accurate measure of γ. A similar analysis can be done to find δ (FIG. 24D).

Figure 25:
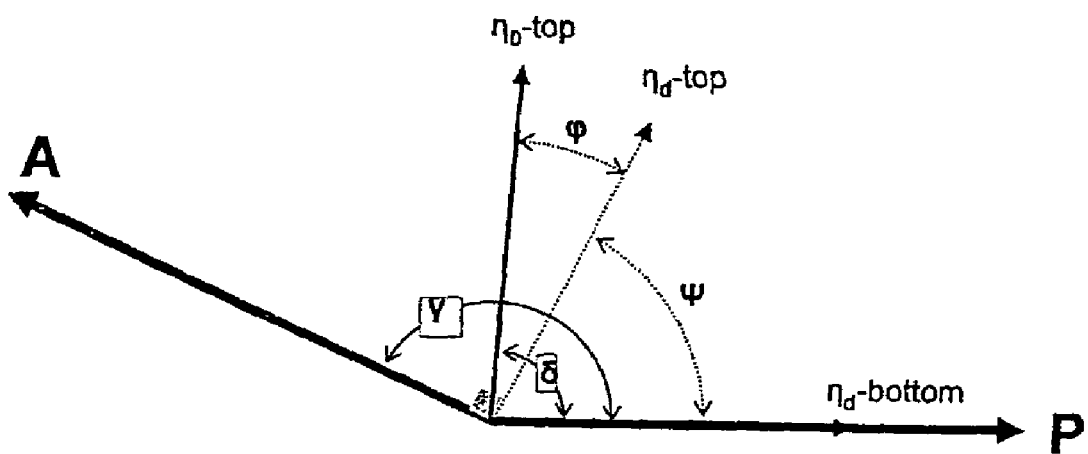
FIG. 25 depicts the angle diagram used to identify $\Psi$ and $\phi$ from the experimentally measured parameters δ and γ.

The angle diagram used to identify Ψ and φ from the experimentally measured parameters δ and γ is shown in FIG. 25. It was assumed that the reference plate has strong anchoring, and so there will be negligible deviation of the director at the bottom surface. The angle γ, measured experimentally, is exactly orthogonal the equilibrium position of the director $\eta_d$-top. Therefore the angle formed between the source polarizer P and $\eta_d$-top, corresponding to Ψ, is (γ−90°). From Part 3 of the described method, one may experimentally determined δ and can then calculate φ=δ−Ψ.

Example 3

Effect of Phosphorylation of Oligopeptides on Surface-Induced Ordering of Nematic Liquid Crystals Liquid crystals (LCs) are soft materials with anisotropic optical and electrical properties. The ordering of molecules within LCs depends sensitively on the topography and chemical functionality of surfaces that confine the LCs. Surface-induced ordering of LCs can propagate as far as 100 μm (~$10^5$ molecular lengths) from by a range of molecular phenomena, including 1) light-induced changes in the conformations of molecules, 2) changes in the oxidation states of surface-immobilized redox-active species, (3) formation of metal-ligand coordination complexes, and 4) specific binding events involving proteins. In the present example, the inventors demonstrate that phosphorylation of oligopeptides immobilized on surfaces can also lead to measurable changes in the ordering of LCs at surfaces. Phosphorylation of proteins is an important physiological event that triggers various cellular activities, including cell division, cell differentiation, and cell secretion.

The present experiments used the 13 residue tyrosine-containing oligopeptide sequence Y1173 (FIG. 26A, top) from the epidermal growth factor receptor (EGFR). EGFR is a transmembrane protein that undergoes autophosphorylation at tyrosine 1173 upon binding of epidermal growth factor. It is associated with cancers with some of the worst prognoses. The inventors use optical methods to characterize the orientational ordering of nematic LCs on surfaces decorated with Y1173, the corresponding phosphorylated EGFR peptide pY1173 (FIG. 26A, middle) and a control peptide in which the tyrosine of Y1173 was exchanged for a phenylalanine (F1173 in FIG. 26A, bottom).

Figure 26:
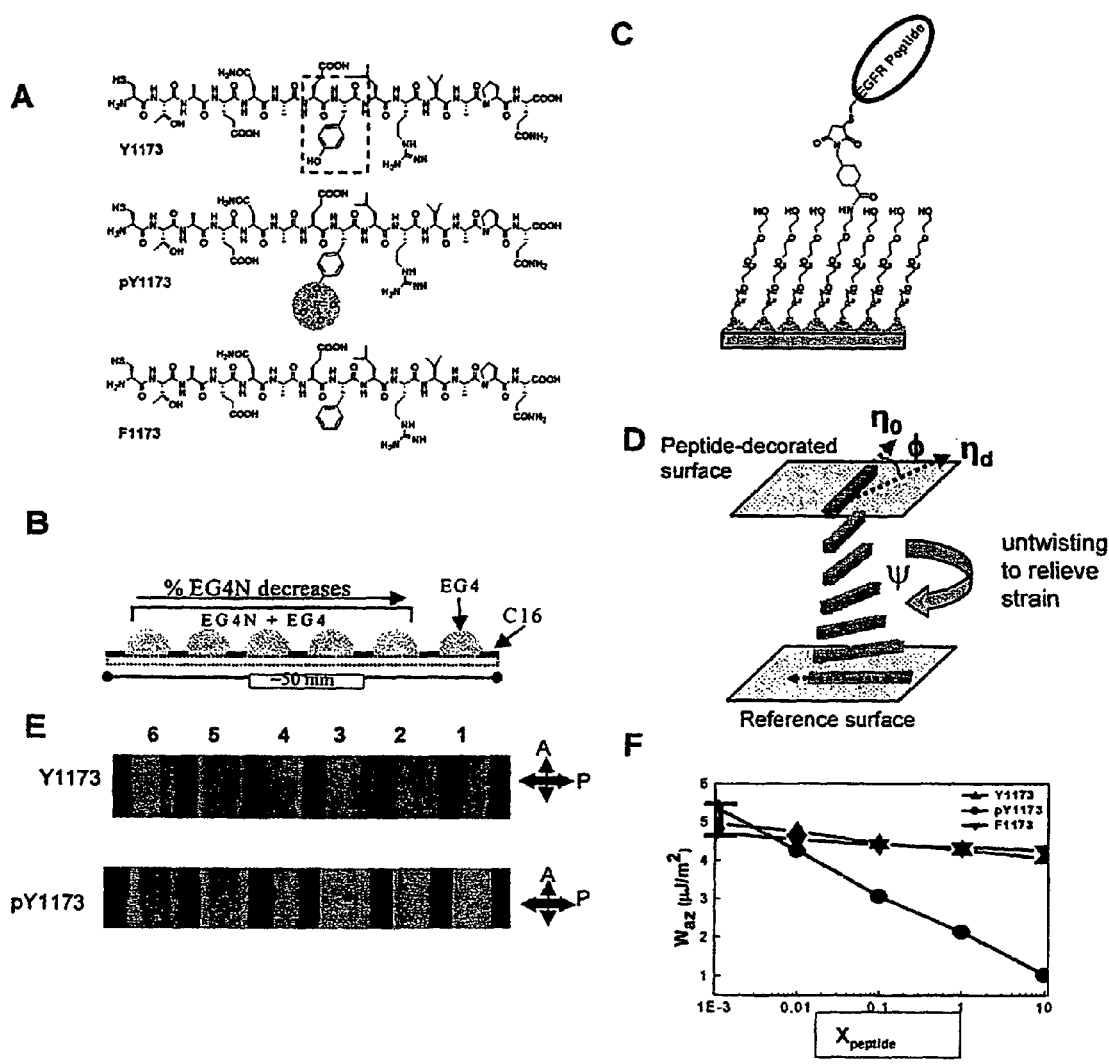
FIG. 26 A) Molecular structures of oligopeptides. From top to bottom, EGFR peptide substrate Y1173; the corresponding phosphopeptide pY1173; a control peptide F1173 in which the tyrosine has been replaced by a phenylalanine. The tyrosine of Y1173 that undergoes phosphorylation to form pY1173 is shown inside the dotted square. (B) Procedure used to pattern peptides in a spatial array that presents different densities of peptides. (C) Chemistry used to immobilize EGFR peptides to gold films. (D) Schematic illustration of the twist distortion of the LC in contact with a peptide-decorated top surface, and a bottom reference surface. (E) Optical micrographs (crossed polars) of LC in contact with surfaces on which peptides were immobilized using concentrations of EGN4 of 0, 0.001, 0.01, 0.1, 1.0 and 10.0 μM for surfaces 1 to 6, respectively: (top) surfaces presenting Y1173 viewed under polarized light microscopy with polarizer parallel to long axis of sample, (bottom) corresponding image for pY1173. A: Analyzer, P: Polarizer. (F) Plot of anchoring energy (W) of LC in contact with surfaces presenting various densities of Y1173 (▲), pY1173 (●) and F1173 (▼). $X_{peptide}$ is the concentration of EG4N in the solution (μM) used to form the mixed monolayers of EG4 and EG4N to which the peptides were covalently attached via the amine group of EG4N.

Gold films (thickness of 20 nm) on which the oligopeptides were immobilized were prepared by physical vapor deposition at an oblique angle of incidence (angle measured from normal $\theta_i$=49°). The structure of these obliquely deposited gold films leads to uniform ordering of LCs. The gold films were patterned with monolayers formed from $CH_3(CH_2)_{15}SH$ (C16) and monolayers prepared from mixtures of $HO(CH_2CH_2O)_4(CH_2)_{11}SH$ (EG4) and $NH_2(CH_2CH_2O)_4(CH_2)_{11}SH$ (EG4N). The ethanolic solutions used to form the mixed monolayers contained 1 mM EG4 and varying concentrations of EG4N (0, 0.001, 0.01, 0.1, 1.0, 10.0 μM) (FIG. 26B). Sulfo-succinimidyl 4-(N-maleimidomethyl)cyclohexane-1-carboxylate (SSMCC, 2 mM) in 0.1 M triethanol amine (TEA) buffer, pH 7.0 was used to activate the primary amines of the EG4N for immobilization of the peptides (250 μM, in 0.1 M TEA buffer, pH 7.0 for 3 hrs). Incubation of the oligopeptides on the activated surfaces lead to their covalent attachment via the cysteine amino acid incorporated into the N-terminal region of each peptide (FIG. 26C). The inventors confirmed immobilization of the peptides on these surfaces by using infrared spectroscopy and ellipsometry.

Surfaces patterned with the oligopeptides were placed face-to-face against a reference gold film ($\theta_i$=64°, C15-functionalized), separated by a 12 μm-thick spacer (Mylar) at one end to create a wedge-shaped cavity. The gold films were oriented such that a twist distortion was generated in the nematic LC 4'-pentyl-4-cyanobiphenyl (5CB) that was drawn into the optical cell by capillary action (FIG. 26D). In the presence of the twist distortion, the LC transmits a mechanical torque to the oligopeptide-decorated surfaces that causes the LC to assume an orientation at these surfaces that depends on the strength of the interactions of the LC with the oligopeptides. Visual inspection of regions 5 (1 μM of EG4N) and 6 (10 μM of EG4N) of the polarized light micrographs (crossed polars) of the LC in FIG. 26E reveals that the LC in contact with immobilized pY1173 appears dark compared to LC in contact with Y1173, qualitatively consistent with the presence of a smaller twist in the LC in contact with pY1173 as compared to LC in contact with Y1173. The gradient in optical appearance evident in region 5 of the pY1173 sample reflect the systematic increase in thickness of the LC across the sample (top to bottom) and the resulting gradient in torque transmitted to the surface by the LC.

The inventors quantified the strength of interaction between the LC and oligopeptide-decorated surfaces by analyzing the experiment shown in FIG. 26E in terms of the azimuthal anchoring energy, W, of the LC on each surface. W characterizes the change in interfacial energy of the LC (σ) with orientation as $\sigma=W \sin^2\phi$, where φ is the orientation of the LC at the peptide-decorated surface ($\eta_{d, Fig\,x}D$) measured relative to the orientation of the LC at the peptide-decorated surface in the absence the twist distortion) ($\eta_0$). The inventors evaluated W using the so-called torque-balance method, as described in previous publications (e.g., Clare, B. H.; Guzman, O.; de Pablo, J. J.; Abbott, N. L., *Langmuir*, 2006, 22, 4654-4659; Ponseca, J. G.; Galerne, Y. *Appl. Phys. Lett.* 2001, 79, 2910-2912, both incorporated herein by reference).

In brief, the anchoring energy of the LC on each peptide-decorated surface was calculated from the expression $W=2K\psi/(d \sin 2\phi)$, where ψ is the twist angle of the LC and, d is the thickness of the LC, and K is the twist elastic constant of the LC (4.22±, 0.5 pN). The inventors measured the anchoring energy at locations in the optical cell where the thickness of LC (determined from interference colors) was d=6.0±0.5 μm. The anchoring energy of the LC in contact with EG4 (no peptide) was determined to be 5.0±0.5 μJ/m² corresponding to φ=10°. FIG. 26F plots W against concentration of each of the peptides on the surfaces. Inspection of FIG. 1F shows that W decreases steadily with concentration of pY1173 whereas the change in W observed for both Y1173 and F1173 is small. These results demonstrate that phosphorylation of the tyrosine of Y1173 at surfaces with $X_{peptide}$>0.01 leads to a quantifiable decrease in anchoring energy of the LC.

In summary, the results presented in this example demonstrate that the ordering of LCs on oligopeptide-decorated surfaces is dependent on the phosphorylation status of the peptides. In related studies (data not shown), the inventors have demonstrated that the immobilized EGFR substrate Y1173 can be phosphorylated by EGFR, and that in situ phosphorylation of Y1173 by EGFR leads to changes in the ordering of LCs. These results provided principles for the development of surface-based methods to detect enzymatic activity (e.g., EGFR tyrosine kinase activity and related molecular mechanisms underlying cancer as well as the action of anti-cancer drugs targeted at EGFR). Current methods for detecting kinase activity generally require complex instrumentation (e.g., mass spectroscopy) or involve tedious procedures such as radio labeling and use of labeled proteins or antibodies.

Example 4

Figure 27:
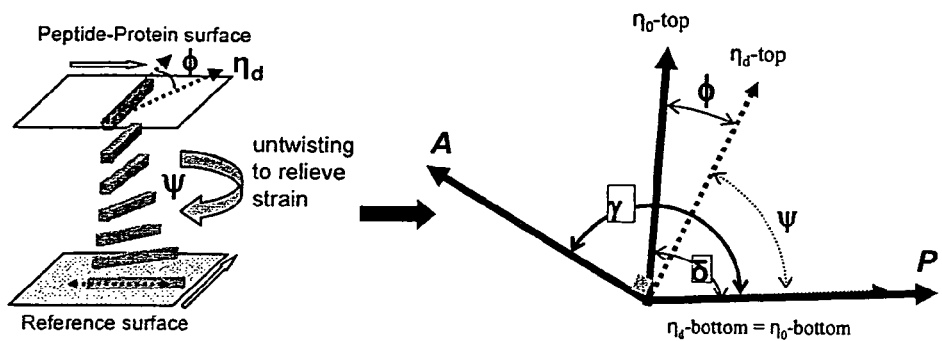
FIG. 27 provides a schematic representation of the modified torque balance method. Note the non symmetrical design: reference plate to have strong anchoring. Where $\phi$=deviation of director ηd from the easy axis η0, $\psi$=twist angle of LC, A: Analyzer, P: Polarizer.

Measuring Anchoring Energy of Nematic Liquid Crystals in Contact with Nanomolar EGFR Phospho-peptide Presented at Interface Using Phospho-specific Antibody The surface induced ordering of liquid crystals to be influenced by the various molecular phenomena occurring at surfaces such as, when in contact with substrates having in-plane anisotropy, LCs can assume a preferred orientation (defined as the easy axis $\eta_0$, FIG. 27) over macroscopic distances. The orientational control of LCs by surfaces is described as anchoring. It is possible to manipulate how strongly the LC prefers that orientation and how much energy is required to perturb the LC away from the direction $\eta_0$. This is defined as azimuthal anchoring energy (W).

In this example, the inventors were focused on the effect of phosphoryl group on EGFR peptide substrate immobilized on the surface such as surface-induced ordering of LCs and associated anchoring energy at very low surface concentration of the peptide. This phosphoryl group induced liquid crystal ordering can be used to study the tyrosine kinase activity and its expression. Epidermal growth factor receptor (EGFR) is a transmembrane glycoprotein possessing EGF-stimulated tyrosine kinase activity, which in turn leads to intracellular substrate phosphorylation and undergoes self-phosphorylation In examples above, the inventors demonstrated the effect of phosphorylation of 13 residue peptide mimic for the region around the major autophosphorylation tyrosine and the Shc binding site (Y1173) of EGFR. The C-terminal tyrosine residues on EGFR, Tyr1173 is one of the major sites of autophosphorylation, which occurs as a result of EGF binding. Once activated, EGFR mediates the binding of the phosphotyrosine binding (PTB) domain of Grb2 through direct interactions with 1068 and Tyr 1086 and through indirect interactions with Tyr 1173 in Ras signaling pathway. Tyr 1173 of EGFR also functions as kinase substrate. Results provided above clearly demonstrated that the presence of phosphoryl group leads to decrease in the twist angle and hence the anchoring energy of the nematic LCs at the interface. Where as such decrease in anchoring energy was not observed with non-phosphorylated peptide and a control peptide. The minimum concentration required to induce the appreciable change in anchoring energy was found to be sub-micromolar range. But it is very important to improve the sensitivity of this technique for the detection of nanomolar to sub-nanomolar phospho-peptide on the surface to use as method for bimolecular material analysis.

Figure 28:
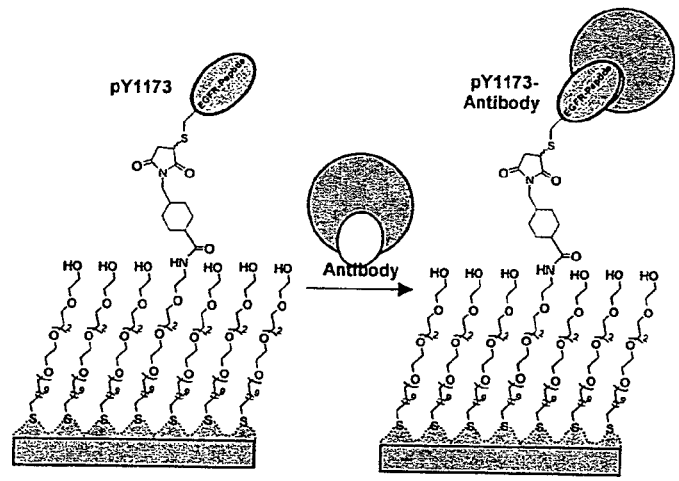
FIG. 28 illustrates antibody binding to a EGFR phosphopeptide immobilized onto a gold film supported on a glass slide using surface chemistry protocols. Gold films were incubated in mixed SAM containing 0.01 μM EG4N in EG4 for 18 hrs. Peptide having cysteine in the N-terminus was covalently attached to the amine terminated oligo (ethylene glycol) SAM in two steps as i) SSMCC in TEA buffer, 45 mins, and ii) EGFR-peptide in TEA, 3.0 hrs (not shown). Protein binding was achieved by treating the peptide surface with monoclonal antiphosphotyrosine (IgG) solution in PBS buffer containing 0.01% Triton B 100 for 1.5 h.

In this example, the inventors report measurements of anchoring energy of 5CB in contact with nanomolar EGFR phospho-peptide using phospho-specific antibody presented on the gold surface, where the phospho-peptide and antibody binding interaction was utilized to enhance the effect of very low concentration of peptides to reduce W of LCs to a measurable quantity (see FIG. 28). This method can serve as a simple technique for the detection of phosphorylation of EGFR peptides at nanomolar concentration and be utilized for determining the expression levels and tyrosine activity of EGFR and its mutants.

Basic principles of this approach are 1) peptide modified surfaces are emerging as useful tools for the study and high through put screening of enzyme activity and capture of protein analyte from complex mixtures, 2) the orientations of LCs near an interface to a confined medium are dictated by the chemical and topographical structure of the interface, 3) the anchoring energy (W) of LCs changes with substrate having different chemical functional group presented at the surfaces 4) binding of phospho-specific antibody to phosphoryl group of EGFR peptide enhance the effect of phospho-peptide at extremely low concentration of peptides and 4) this technique is simple and does not require any sophisticated, expensive instrumentation. The principal aims of the work reported here are to improve methodology to measure the change in anchoring energy of nematic LCs in contact with peptide immobilized onto the substrate with increase in sensitivity to nanomolar peptide utilizing the peptide-protein interactions. Accordingly, determination of the peptide at very low concentration at which peptide alone cannot effective enough to reduce anchoring energy of LCs. Secondly to determine the minimum amount of protein required to saturate the peptide surface.

2. Materials and Method

All materials were used as received unless otherwise noted. Fisher's Finest glass slides were obtained from Fisher Scientific (Pittsburgh, Pa.). Gold 99.999% purity was obtained from International Advanced Materials (Spring Valley, N.Y.). Titanium 99.99% purity was obtained from PureTech (Brewster, N.Y.). Tetraethylene glycol-terminated thiol (EG4) and corresponding amine-terminated thiol (EG4N) as a hydrochloride salt were obtained from Prochimia (Gdansk, Poland). The sulfo-succinimidyl 4-(N-maleimidomethyl)cyclohexane-1-carboxylate (SSMCC) linker was obtained from Pierce Biotechnology (Rockford, Ill.). Nematic Liquid crystal 4'-pentyl-4-cyanobiphenyl (5CB) was obtained from EM Industries (New York, N.Y.) sold under the trademark name Licristal® (K15). Triethanolamine (TEA) was obtained in 99% purity from Fisher. Peptides were obtained from the University of Wisconsin, Biotechnology Center. The purity of the peptides was found to be more >98% as determined by analytical HPLC and their integrity was again confirmed by MALDI-TOF. Monoclonal anti-phosphotyrosine IgG was obtained from Sigma Aldrich. Ethanol (200-proof) was obtained from Aaper Alcohol (Shelbyville, Ky.) and purged with argon gas prior to use. Polydimethylsiloxane (PDMS) elastomeric stamps were prepared using Sylgard® 184 silicone elastomer kit obtained from Dow Corning (Midland, Mich.). All other materials were obtained from Sigma-Aldrich unless otherwise noted.

Preparation of Gold Surfaces. Obliquely deposited gold films (20 nm in thickness) on piranha cleaned glass slides were prepared according to reported procedure. As these gold films are semi-transparent, PM-IRRAS and ellipsometric thickness measurements were performed using reflective gold films prepared by sequentially depositing 10 nm of Ti and 200 nm of Au onto silicon wafers (Silicon Sense, Nashua, N.H.) at normal incidence. All gold samples were used within a week of preparation.

Formation of Patterned Mixed Self-assembled Monolayers (SAMs). A polydimethylsiloxane (PDMS) elastomeric stamp with raised features (having dimensions of 2-3 mm width and 2-3 mm height) was cast from an aluminum master. The stamp was inked with a 2 mM ethanolic solution of hexadecanethiol (C16) and then gently dried using a stream of nitrogen gas. The stamp was placed in conformal contact with the obliquely deposited gold film for 10 seconds. Next, 1 mM solutions of mixed oligo(ethylene glycol)-terminated thiols (EG4N-amine terminated+EG4) were prepared using argon purged ethanol. These solutions were stored under an argon atmosphere to prevent oxidation of the sulfhydryl functionality. Droplets of thiol solutions were applied to the gold substrate, confined between the patterned stripes of C16 SAMs. The substrates were stored in a chamber saturated with ethanol vapor (to prevent droplet evaporation) for 18 hours, and then rinsed with copious amounts of water and ethanol, and then gently dried under a stream of nitrogen gas Preparation of Patterned Peptide Modified Array. The Chemistry Used to Attach peptides to oligo(ethylene glycol)-containing SAMs is described in our previous publications. Patterned mixed-SAMs array comprised of EG4N and EG4 was prepared as explained in the previous section, using 1 mM ethanolic solutions of thiols (EG4N+EG4). After 18 hour SAM functionalized surface was rinsed with copious amounts of ethanol, water and dried under stream of nitrogen gas. 2 mM solutions of hetero-bifunctional linker sulfo-SMCC (in 0.1 M triethanolamine buffer, pH 7.0) were applied as droplets on to the monolayers for 45 min. These surfaces were rinsed gently in water and dried under nitrogen gas. Solutions of cysteine-terminated EGFR peptide substrates (250 μM) in 0.1 M triethanolamine (TEA) buffer, pH 7.0 were applied as droplets on to mixed-SAM functionalized regions. The substrate was stored in a chamber saturated with water for 3 h. These surfaces were rinsed (2×) with 0.1 M triethanolamine buffer containing 0.1% triton B 100 for 5 min., washed with water and dried under nitrogen gas.

Protein Binding Studies using EGFR Peptide Surfaces. Monoclonal anti-phosphotyrosine IgG in PBS+0.05% TX was applied to the peptide surfaces for 1.5 h. The sample was stored in a chamber saturated with water. All samples were rinsed (3×) for 5 min. in PBS+0.05% Triton-X 100, washed with water, and finally dried under a stream of nitrogen gas prior to use.

Preparation of Optical Cell with Wedge Shaped Geometry. Optical Cell was Prepared by using patterned array surface and reference plate. Reference plate with strong anchoring was prepared by immersing an obliquely deposited gold surface ($\theta i=64°$) in 2 mM solution of pentadecanethiol (C15) for 2 h rinsed with copious amounts of ethanol and dried under a stream of nitrogen gas. The patterned peptide array surface treated with antibody was placed face-to-face against the reference plate, such that in-plane direction of gold deposition of the reference plate was rotated approximately 90° relative to that of the top surface (FIG. 4A). The surfaces were separated by a 12 μm spacer at one end, no spacer at the other end, to create a wedge-shaped cell. The optical cell and 5CB were both warmed to approximately 40° C. (above the clearing point for 5CB). 5CB was then drawn into the optical cell by capillary action. The sample was slowly cooled to room temperature. Measurements of the optical properties of the LC film for all samples were taken after 30 minutes of cooling to room temperature (22° C.), as both temperature and age of the sample (surface gliding) are known to influence the measured anchoring strength.

Optical determination of d, δ, Ψ and φ. The optical method used to determine the thickness (d), angle formed between the easy axes of each confining substrate (δ), the angle over which the LC forms a twist (ψ), and the angle of deviation of the director from the easy axis (φ) was previously outlined. Measurements were recorded using a polarized light microscope (BX 60, Olympus) equipped with an X-Y translating stage and fitted with a digital camera for image capture.

Ellipsometry. A Rudolph AutoEL ellipsometer (wavelength of 632 nm, 70° angle of incidence) was used to determine the optical thickness of the SAMs, EGFR peptide substrate and protein bound to peptide on the surfaces of 2000 Å thick gold films. Ellipsometric constants were determined at five locations on each sample. A simple slab model was then used to interpret these constants. The slab (SAM, peptide and protein) was assumed to have an index of refraction of 1.46.

PM-IRRAS. IR spectra of EGFR peptide substrate presented on gold films (thickness of 2000 Å) were recorded using a Nicolet Magna-IR 860 FT-IR spectrometer with photoelastic modulator (PEM-90, Hinds Instruments, Hillsboro, Oreg.), synchronous sampling demodulator (SSD-100, GWC Technologies, Madison, Wis.) and a liquid Nitrogen-cooled mercury cadmium telluride (MCT) detector. All spectra were taken at an incident angle of 83° with the modulation centered at 1600 $cm^{-1}$. For each sample, 500 scans were taken at a resolution of 4 $cm^{-1}$. Data was collected as differential reflectance vs. wave number and spectra were normalized and converted to absorbance units via the method outlined in Frey et al., *Polarization-Modulation Approaches to Reflection-Absorption Spectroscopy. In Handbook of Vibrational Spectroscopy*; Griffiths, P. R., Ed.; John Wiley & Sons: New York, 2002; Vol. 2; pp 1042, incorporated herein by reference.

Image capture and luminosity analysis. Images of the optical appearance of the liquid crystals were captured with a digital camera mounted on a polarized light microscope (BX60, Olympus). Consistent settings of both the microscope light source (aperture set at ½ maximum, and lamp intensity also set at ½ maximum), digital camera (2.8 f-stop, 1/200 shutter speed) and optical zoom 4× allowed for the direct comparison of images taken of different samples. The images were taken at optical zoom 20× for determining angles γ and δ. To quantify the luminosity of the liquid crystal in contact with the peptide-protein arrays, each composite image was converted to a grayscale image. The average pixel brightness of a region was calculated, assigning a completely black pixel the value of 0 and a completely white pixel receives the value of 255.

Figure 30:
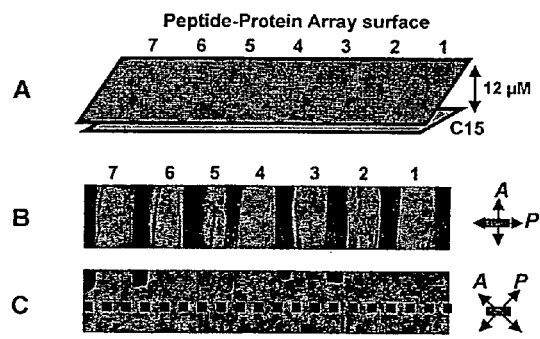
FIG. 30 provides in A) pictorial representation of optical cell prepared from Patterned peptide-antibody array surface (top) and a reference plate (bottom) showing the peptide regions treated with different concentration of antibody. B) Polarized light microscope images of the peptide-antibody array sample a) viewed under polarized light microscopy with polarizer and analyzer are perpendicular to each other and b) when both polarizers were rotated to 45° with respect to the sample. A: Analyzer, C) Polarizer. Gray dotted line indicate the position (constant thickness d=6.0±0.5 μm, as determined from Michel-Levy chart) at which all measurements were made.

Preparation and Characterization of Peptide-Modified Interfaces: Gold films were prepared by evaporating Au (20 nm) at an angle of incident on to a glass slide coated with 8 nm Ti according to the reported procedure (Skaife, J. J.; Abbott, N. L. *Chem. Mater.* 1999, 11, 612). Patterned gold surface ($\theta i=49°$) was prepared by contact printing 2 mM hexadecanethiol in ethanol on to the surface using PDMS stamp. The surface was washed with ethanol and dried under nitrogen gas. Two-component SAMs on gold film were prepared using thiols EG4N and EG4. Mixed SAM solution was prepared such that the solution composition is 0.01 µM EG4N in 1 mM EG4. The neutral EG4 SAMs were used as they are known to resist non-specific adsorption of biomolecules such as proteins. The mixed SAM solutions were applied in the regions 2-7 confined between C16 regions (FIG. 28) for 18 hrs. Co-adsorption of thiols having similar structure and length is unlikely to lead to segregation of species within the mixed SAM. Region 1 (FIG. 30) was functionalized with neutral EG4 SAM. The array surface was washed with ethanol, water and dried under nitrogen gas. Regions 2-7 were then treated with the 1 mM solution of hetero-bifunctional linker sulfo-SMCC in TEA buffer (see Materials and Methods), after 45 min. washed with water and gently dried under nitrogen gas. Solutions of EGFR peptides pY1173 (Regions 3-7) and control Y1173 (Region 2) in triethanolamine buffer were applied to the regions functionalized with sulfo-SMCC in a closed chamber saturated with water to minimize the evaporation of peptide solution. After 3.0 h, the surface was rinsed (2×) with TEA+0.1% triton B 100 for 10 min. to remove any unreacted peptides present on the surface. The surface was washed with water and then dried under stream of nitrogen gas. Immobilized peptides on the gold surface was characterized using Polarization Modulation-Infrared Reflectance Absorbance Spectroscopy (PM-IRRAS) and also by ellipsometric optical thickness measurements as reported in our previous publications. PM-IRRAS is a surface-sensitive analytical technique that can provide information about relative quantity and type of organic functional groups present on the surface. Strong absorption bands are observed for the maleimide asymmetric ($1707$ $cm^{-1}$) and symmetric ($1745$ $cm^{-1}$) stretching modes. The inventors observed bands in the $1670$ $cm^{-1}$ region, corresponding to the Amide I stretching mode and at $1537$ $cm^{-1}$ corresponding to amide II absorption which are characteristic of a peptide.

The peptide array was then treated with monoclonal antibody antiphosphotyrosine (IgG). Regions 3-7 containing pY1173 was treated with antibody solutions in PBS+0.05% Triton B 100 buffer containing 0.01, 0.1, 1, 10, and 100 nM respectively (see table in FIG. 30). The control region having Y1173 was treated with 100.0 nM antibody. After 1.5 h, the surface was rinsed with PBS+0.05% Triton B 100 (2×), washed with water and dried under nitrogen gas. Rinsing the surface with buffer having surfactant was crucial to remove unbound protein. Antibody binding to the phospho-peptide pY1173 was characterized and confirmed by ellipsometric optical thickness measurements.

A reference plate was prepared with gold film evaporated on to the glass slide at an oblique deposition angle 64°. Reference plate was homogeneously functionalized with pentadecane thiol (C15) by immersing in 2 mM ethanolic solution for 2 h. The surface was washed with ethanol and then dried under nitrogen gas. Optical wedge cell was prepared as explained in Materials and methods section. 5CB was introduced in to the cell by capillary action. The sample was placed on X-Y stage of the polarized light microscope. Microscope settings were set as brightness at 6, light source 50%, digital camera zoom 4×, exposure time ½₀₀" and aperture 2.8f. The sample was imaged as several pictures under these settings and were stitched together to get the complete sample image with analyzer and polarizer perpendicular to each other and rotated 45° relative to the sample (FIG. 30B). All the optical measurements were made at 5CB film thickness $6.0\pm0.5$ µm along gray dotted line (FIG. 30C) as determined by comparing the interference patterns observed to that in the Michael Levy chart.

Figure 29:
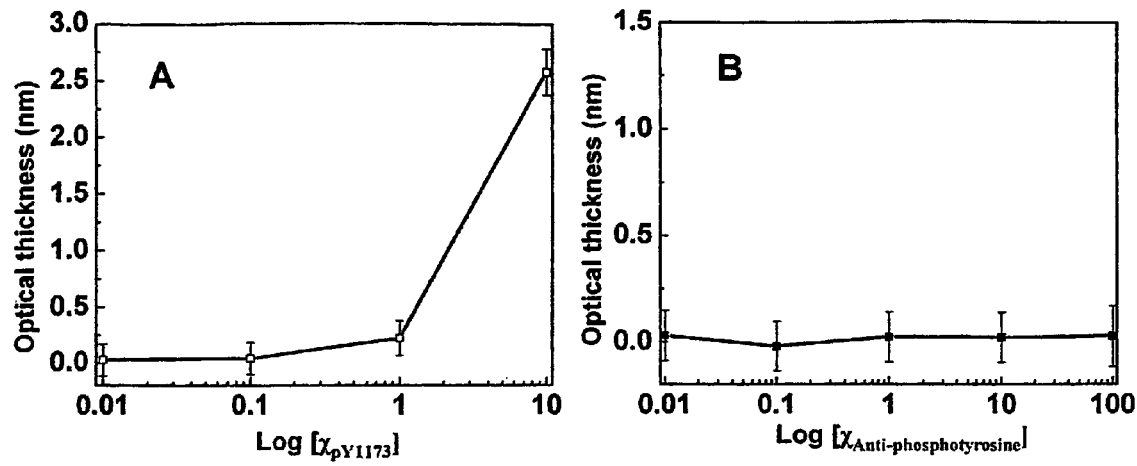
FIG. 29 depicts in A) optical thickness of the surfaces having pY1173-antibody, prepared by immobilizing pY1173 using solutions of 0.01, 0.1, 1.0 and 10.0 μM followed by treating with monoclonal antiphosphotyrosine (IgG, 100 nM). B) Optical thickness of 0.01 μM pY1173 immobilized surfaces treating with various concentrations of antibody (0.01, 0.1, 1.0, 10 and 100 nM in PBS+0.01% Triton B 100 buffer). $\chi pY1173$=concentration of pY1173 in μM. $\chi$Antiphosphotyrosine=concentration of monoclonal antiphosphotyrosine (IgG) in nM.

Ellipsometric Optical Thickness Measurements of Antibody Treated Peptide Surface: The inventors have performed ellipsometric optical thickness measurements of peptide surfaces containing various amounts of pY1173 from 0.01 to 10 which were treated with 100 nM antiphosphotyrosine (IgG) antibody (FIG. 29A). An optical thickness of 2.6 nm was observed with surface immobilized with 10 µM pY1173 (1%) upon treatment with 100 nM antibody and optical thickness decreases to 0.22 nm for an antibody treated peptide surface immobilized with 1.0 µM pY1173 (0.1%). No appreciable optical thickness was measured for peptide surfaces immobilized with 0.1 and 0.01 µM pY1173. The inventors also measured optical thickness of peptide surface immobilized with 0.01 µM pY1173 with varying amounts of antibody (0.01 to 100 nM). No net change in optical thickness was observed on these surfaces (FIG. 29B). These results indicate that 1.0 µM is the lower concentration limit of pY1173 that can be detected with ellipsometry where as 0.01 µM pY1173 presented on the gold surface can be detected using peptide binding agents such as antibody.

Anchoring Energy of LC in Contact with Peptide-Protein Presented at Surface: The inventors applied the previously reported torque balance method to determine the anchoring energy of nematic 5CB in contact with protein bound to EGFR phospho-peptide at very low surface concentration. LCs in contact with 0.01 and 0.001 µM pY1173 was found to possess anchoring energy of 4.7 and 4.6 $\mu Jm^{-2}$ (deviation $\phi=10.0$ and 11.0) against 5.2 $\mu Jm^{-2}$ (10.0) for the control region having EG4 SAM. The change is not sufficient enough as compared to that of control region and may not attribute to the presence of phospho-peptide on the surface. These results clearly shown that Region on the array surface treated with 0.01 µM phospho-peptide is the lower concentration limit beyond which no change in W was observed. The inventors' aim was to improve sensitivity of the technique to render the detection limit of pY1173 in the range of nanomolar to sub-nanomolar by treating these regions with external peptide binding agents. The inventors have found that pY1173 below critical concentration can be made effective by treating with protein which can bind to phosphoryl group of the peptide and hence induce large change in anchoring energy. The inventors have treated the low density peptide surface (prepared by incubating with 0.01 and 0.001 µM pY1173) with 100 nM phospho-specific antibody. Anchoring energies were found to be 1.4 and 2.9 $\mu Jm^{-2}$ accompanied by decrease in the 'W' of 3 and 2 $\mu Jm^{-2}$ units respectively. These results increase the lower detection limit of the surface immobilized phospho-peptide to a nanomolar range. The inventors then standardized this technique to determine minimum concentration antibody required to saturate the low density phophopeptride surface. In a subsequent experiment, pY1173 concentration was fixed to 0.01 µM and antibody concentration was varied from 100 to 0.01 nM (100, 10, 1.0, 0.1. 0.01 nM). Also included are the regions having 0.01 µM Y1173 (Region 2) and EG4 (Region 1) for control studies.

The inventors assembled an optical cell comprised of antibody treated patterned peptide array surface and a reference plate, as shown in FIG. 30A. 5CB was warmed to its clearing point, introduced into the optical cell by capillary action, and then cooled to room temperature prior to analysis. FIG. 30B shows the visual appearance of the sample imaged under polarized light microscope. Similar to our earlier findings, the use of patterned substrates leads to patterned structures of LC that can be individually addressed. The observed a difference in the brightness of LC in contact with peptide regions treated with different amounts of antibody. Region 1, where in LCs in contact with the EG4 SAM ($\chi_{peptide}=0$), the LC appears bright when viewed by cross-polarized light microscopy. Brightness in the region having Y1173 also similar to that in Region 1 having no analyte but only EG4. Moving from right to left, LC in contact with Regions 3-7 having treated with increased amount of antibody ($\chi_{Antiphosphotyrosine}$=0.01, 0.1, 10, 100 nM), brightness decreased (see Supporting Material) as an indicative of gradual decrease in the twist of LC structure. Brightness in the Regions 5 and 7 was not completely diminished but shown some brightness attributed to the presence of defects. The phosphopeptide in these regions were saturated with antibody and is sufficient enough to change orientation of liquid crystals to induce defects. The halo effect of these defects makes these regions brighter than the actual appearance. The overall decrease in intensity of regions 3-7 was confirmed from the high resolution images captured from these regions. High resolution images of antibody treated peptide regions shown that brightness decreases gradually from Region 3 to 7.

The azimuthal anchoring energy of the surface is estimated using a torque-balance model (Fonseca, J. G.; Galerne, Y. *Appl. Phys. Lett.* 2001, 79, 2910; Polossat, E.; Dozov, I. *Mol. Cryst. Liq. Cryst.* 1996, 282, 223.; Wood, E. L.; Bradberry, G. W.; Cann, P. S.; Sambles, J. R. J. *Appl. Phys.* 1997, 82, 2483; derived from the Rapini-Papoular approximation (Rapini, A.; Papoular, M. J. Physique. Colloq. (France) 1969, 4, 54), of surface anchoring torque) and can be described by the following expression W=2K$\psi$/d sin(2$\phi$)–(1), where K is the twist elastic constant for the LC, is the thickness of the film of LC of study, and $\psi$ is the twist angle over which the LC is distorted. The use of a reference plate permits the study of patterned surfaces, enabling the determination of 'W' for multiple concentrations peptide or different peptides arrayed onto a single substrate, thus minimizing the volume of valuable solutions of biological materials required for surface functionalization and analysis. Specifically, the inventors apply this methodology to the study of how incremental addition of peptides or proteins bound to peptides at interfaces can lead to changes in 'W' of a substrate.

Figure 31:
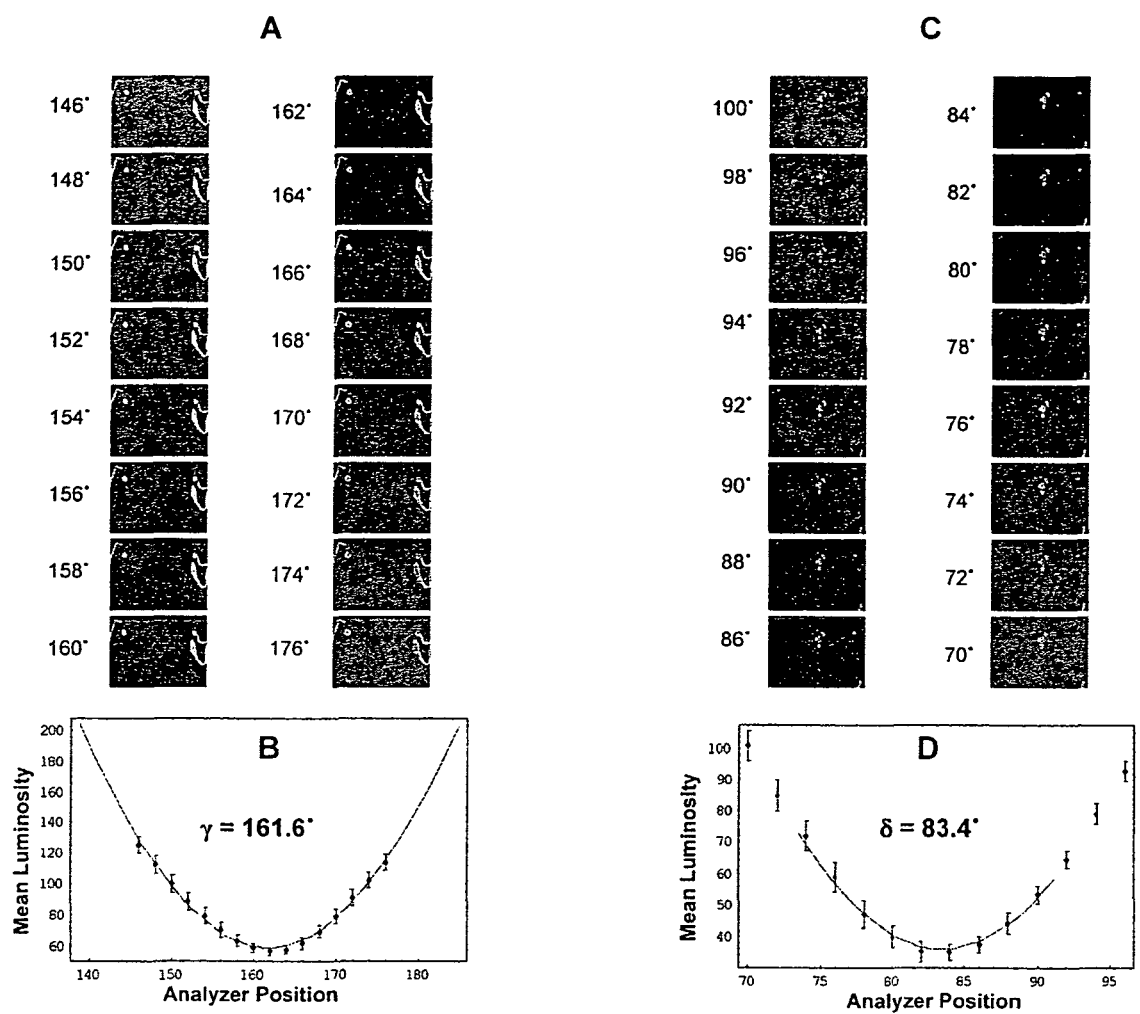
FIG. 31 illustrates the optical method for determination of angles γ and δ of the antibody treated peptide array sample (for Region 3 of the array sample). A and C: Grayscale polarized light images captured as a function of analyzer position for twisted and hybrid regions, respectively. B and D) Plots of grayscale luminosity of images to determine the analyzer position at which minimum of light is observed.

The angles $\gamma$ and $\delta$ were determined from gray scale analysis of the images shown in FIG. 31 as explained in Materials and Methods section. Twist angle ($\psi$) and deviation ($\phi$) of top-director from the easy axis were calculated using experimentally determined values of $\gamma$ and $\delta$. The anchoring energy of LCs in the regions 1-7 were calculated from the experimentally determined values of $\psi$ and $\phi$, thickness of the LCs film at which all measurements were made (along gray dotted line, FIG. 30C) and known value of elastic torque constant K using equation 1.

Figure 32:
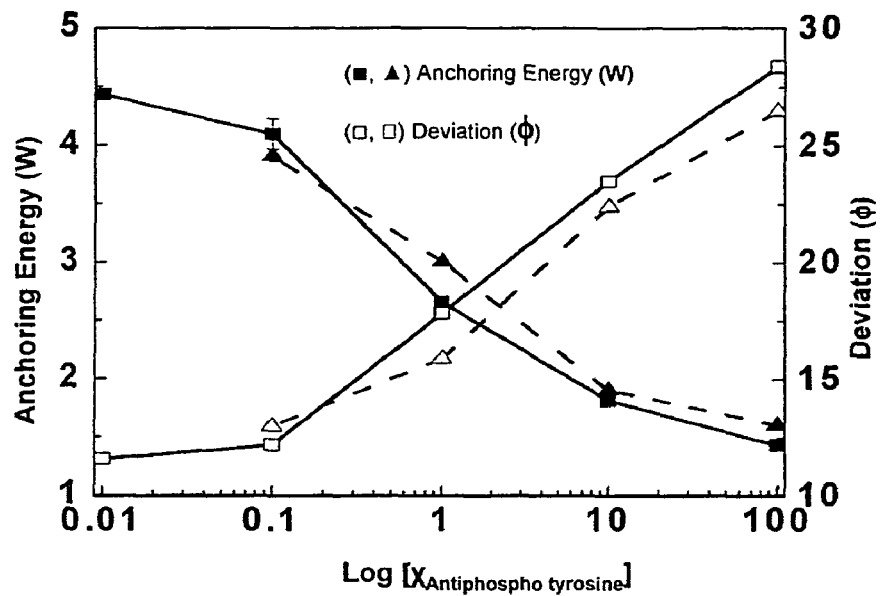
FIG. 32 provides a plot of anchoring energy (■, ▲) and deviation (□, ◻) of LCs in contact with EGFR phosphopeptide pY1173 (0.01 μM) bound to different concentration of monoclonal antiphosphotyrosine (IgG). $\phi$=deviation of top director $\eta d$ from the easy axis $\eta 0$ (in degrees). $\chi$Antiphosphotyrosine=concentration of monoclonal antiphosphotyrosine (IgG) in nM. W=anchoring energy in μJ/m2.

Data from the table provided in FIG. 32 shows that there is a gradual decrease in anchoring energy of liquid crystals in contact with 0.01 $\mu$M pY1173 treated with antibody of varying concentrations from 0.01 to 100 nM (Region 3-7). Anchoring energy of LCs in contact with 0.01 $\mu$M pY1173 was plotted against anti-phosphotyrosine concentration (FIG. 32) on logarithmic scale. FIG. 32 shows that there exists a linear relationship between anchoring energy of liquid crystals and concentration of anti-phosphotyrosine. Region 7 treated with 100 nM antibody changed the anchoring energy of LCs to 1.4 $\mu$J/m$^{-2}$ ($\phi$=28°) against 5.0 $\mu$J/m$^{-2}$ ($\phi$=10°) for control Regions 1 and 2. Regions 6 and 7 shown comparable values for W (1.8 and 1.4 $\mu$J/m$^{-2}$) indicate that 10 nM antibody is enough to completely saturate the 0.01 $\mu$M phosphopeptide regions. Also an important observation is that 0.01 and 0.1 nM antibody concentration are able to induce decrease in anchoring energy of LCs in contact with 0.01 $\mu$M pY1173 from 5.0 $\mu$J/m$^{-2}$ (for Regions 1 and 2 with EG4 and Y1173) to 4.4 and 4.0 $\mu$J/m$^{-2}$ respectively. To determine the experimental error involved in anchoring energy measurements, in subsequent experiment the inventors have treated the Regions 3-7 with 0.1 nM antibody and anchoring energies corresponding to the regions 3-7 were measured. Standard error of the mean was calculated using the anchoring energies of the regions 3-7 and included as error bar for the corresponding data point at 0.1 nM antibody concentration in FIG. 32.

The results presented in this example demonstrate that phospho specific antibody can be effectively used to measure the anchoring energy of LCs in contact with of very low concentration of EGFR phosphopeptide immobilized on the surface. The concentration of antibody solution used to treat 0.01 M phosphor-peptide to effect the change in anchoring energy was found to be of picomolar range. These results indicate that nanomolar concentration of phospho peptide can be detected using picomolar phospho specific antibody.

Example 5

Utilizing Anchoring Energy Measurements to Detect an Analyte Delivered to a Surface by using Affinity Contact Printing Protein molecules were specifically captured and transferred to another surface using an affinity microcontact printing procedure described in U.S. patent application Ser. No. 10/711,517, filed Sep. 23, 2004, incorporated herein by reference. Briefly, a gold surface was produced by electron beam evaporation at an angle of incidence of 40°. This surface was functionalized with HSC$_{11}$-EG4NH$_2$ immediately after removal from the vacuum chamber of the electron beam evaporation system. A polydimethysiloxane (PDMS) stamp with micron scale features was chemically functionalized using oxygen plasma. The hydroxyl groups created by the oxygen plasma were then functionalized with aminopropyl-triethoxysilane to yield exposed primary amine groups. To these amines, succinic anhydride was attached to yield a group suitable for standard NHS/EDC attachment of an antibody molecule. Affinity purified mouse anti-biotin molecules were attached to the PDMS stamp using NHS/EDC chemistry and blocked with SuperBlock buffer containing 0.05% tween-20. After blocking, the stamps were incubated with either biotinylated BSA molecules or unmodified BSA. After this incubation step, the stamps were washed and thoroughly dried before stamping onto the obliquely deposited gold surface.

Another surface (the reference plate of the twist cell) was produced by evaporating gold at a 60° angle of incidence to a glass surface. This surface was then functionalized with HSC$_{15}$. A liquid crystal cell was then assembled by sandwiching liquid crystal between the two gold substrates. The gold substrates are held apart by a thin (~12 $\mu$m) spacer and oriented such that the easy axes of the liquid crystals on the gold surfaces are perpendicular to one another.

Figure 33:
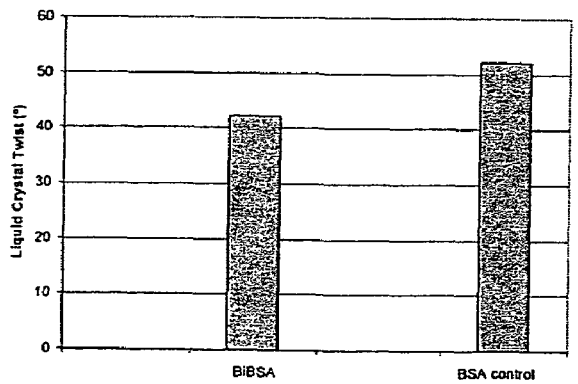
FIG. 33 depicts a bar chart showing twist angles averaged over the area of stamped surfaces.

The orientation of the liquid crystal molecules is quantified with the use of a polarizing microscope which reports the orientation of the liquid crystal molecules at the protein stamped surface. The background regions are distinguishable from regions where protein was stamped because the liquid crystal twist will be disrupted by the presence of proteins. FIG. 33 shows average orientations from the stamps that were incubated with biotinylated BSA and the unmodified BSA control. In the absence of the use of the twisted cell, the presence of the biotinylated BSA on the stamps was not optically detectable.

Example 6

Assembly of LC-polyelectrolyte Multilayer Droplets and Anchoring Energy Measurements Based Thereon The LC-in-water emulsions are formed by sonicating a mixture of 1 vol. % 5CB in an aqueous solution of a strongly charged polyelectrolyte, poly(styrene sulfonate) (PSS) (1 mg mL$^{-1}$). The LC droplets are spherical, with a size range of 1-10 µm and are visually observed to be stable against coalescence for months. The droplets are size separated into populations comprised of 1-2 micrometers, 2-5 micrometers and 5-10 micrometers by sedimentation. The polyelectrolytes for layer-by-layer assembly are deposited from 1 mg mL$^-$ solutions containing 0.1 M NaCl and either polyallyamine hydrochloride (PAH) oe PSS. Multilayers comprised of 15 bilayers are prepared. The optical appearance of the LC (nematic 5CB) is recorded by using polarized light microscopy. Next, an analyte that interacts with the PEM and/or liquid crystal is introduced into the system. In this example, the analyte is sodium dodecylsulfate. The optical appearance of the droplets is observed using the polarized light microscope. It is observed that the optical appearance of the droplets changes in a manner that depends on the size of the LC droplets. By recording the time at which droplets change their optical appearance, a method to quantify the concentration of analyte in solution is established. The final optical appearance of the droplets of LC is also made. The transition time and orientation of the LC is influenced by the anchoring energy of the LC at the surface of the droplets and the elastic energy stored in the LC confined within the droplet.

Example 7

Measurement of Enzymatic Activity by LC-lipid Droplets

Figure 34:
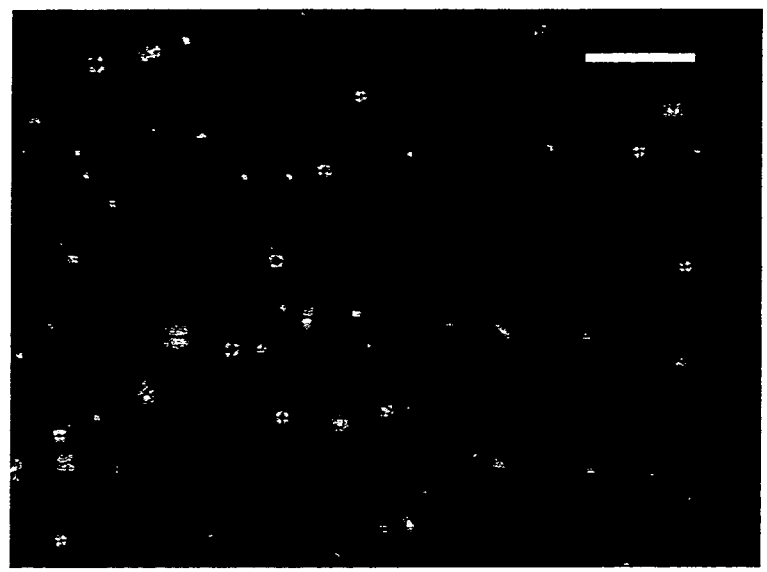
FIG. 34 provides in A) a cross-polarized image of 5CB-DLPC emulsions in DI water. Scale bar 50 μm, B) a cross-polarized image of 5CB-DLPC emulsion in DI water. Scale bar 10 μm, C) a cross-polarized image of 5CB-DLPC emulsions in TBS-Ca buffer (10 mM tris, 20 mM NaCl, 5 mM $CaCl_2$). Scale bar 50 μm, D) a cross-polarized image of 5CB-DLPC emulsions after incubation in TBS-Ca buffer (10 mM tris, 20 mM NaCl, 5 mM $CaCl_2$) for 20 hours. Scale bar 50 μm, E) a cross-polarized image of 5CB-DLPC emulsions after incubation in TBS-Ca buffer (10 mM tris, 20 mM NaCl, 5 mM $CaCl_2$) with ~0.7 μM $PLA_2$ for 20 hours. Scale bar 50 μm.
Figure 34:
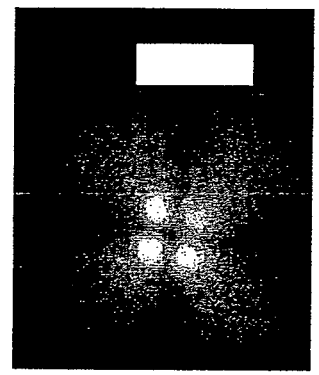
Figure 34:
Figure 34:
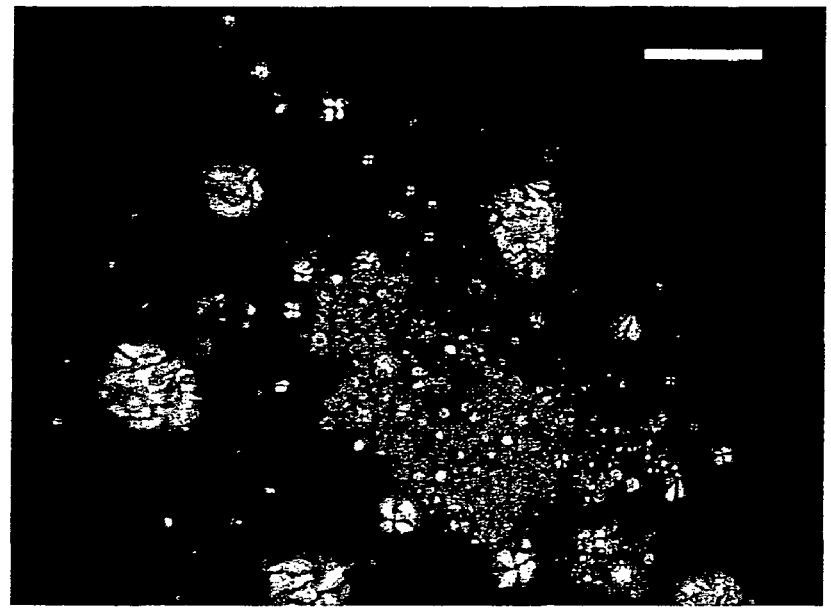
Figure 34:

This example describes the measurement of phospholipase A$_2$ by LC-phospholipid droplets. A vial of dried DLPC was stored in the freezer at −20 C and DI water was added to the vial such that a 250 µM DLPC solution was formed and allowed the lipid to resuspend in the DI water for 1 hour. In addition the lipid was vortexed once, using a using a Fisher Vortex Genie 2 on vortex level 8 for ten seconds, after the addition of DI water and then once again after an hour. 5CB was added to the lipid solution to give a 1 vol. % 5CB solution, this mixture was then vortexed followed by sonication for 30s at a power of 3 W. Then 0.75 ml of emulsion and 0.75 ml of DI water was added to a 1.5 ml Eppendorf tube. The tube was then vortexed followed by centrifugation at 5000 g for 5 min. This resulted in a pellet forming at the bottom of the tube. Next 0.75 ml of the supernatant was removed and replaced with 0.75 ml of water. This procedure was repeated 3 times. The emulsions were then imaged by placing a droplet of the emulsion solution onto a microscope slide and covering the droplet with a cover slip. (FIGS. 34A and B) Next, the emulsions were suspended in TBS-Ca buffer by centrifuged the samples and removing the supernatant and replacing it with TBS-Ca buffer following the above conditions. The emulsions were again imaged following the procedure mentioned above. (FIGS. 34C and D) Some of the samples were then treated with PLA$_2$ by adding a 10 µl droplet of 100 µM PLA$_2$ into the Eppendorf tube creating ~0.7 µM solution. The samples were vortexed after the PLA$_2$ was added and then imaged after 20 hrs of incubation with the PLA$_2$. (FIG. 34E) The emulsion solution was initially cloudy after being formed in DI water and then exchanged for the TBS-Ca buffer, however after the incubation with PLA$_2$ the solution was clear and liquid crystal droplets could be seen. This example demonstrates the utility of LC droplets in the bio-analyte detection context.

Those skilled in the art will recognize, or be able to ascertain using no more than routine experimentation, numerous equivalents to the specific materials and methods described herein. Such equivalents are considered to be within the scope of this invention and encompassed by the following claims.

What is claimed is:

1. A method for detecting an analyte in a sample, comprising:
   (a) contacting the sample with a substrate surface that defines a first easy axis when in contact with liquid crystal;
   (b) providing a reference surface that defines a second easy axis when in contact with liquid crystal such that the substrate surface faces but is spaced apart from said reference surface, and wherein the easy axis of the substrate surface and the easy axis of said reference surface are rotated from one another by a known angle that is not zero;
   (c) introducing a liquid crystal between the reference surface and the substrate surface; and
   (d) measuring the departure of the orientation of the liquid crystal from the easy axis of the substrate surface, wherein a non-zero departure indicates the presence of the analyte in the sample.

2. The method according to claim 1 wherein the sample is contacted with the substrate surface with an affinity stamp by affinity micro-contact printing.

3. The method according to claim 1 wherein said reference surface and said substrate surface form a wedge-shaped cavity in which is positioned said liquid crystal.

4. The method according to claim 1 wherein the analyte is a biomolecule, an assembly of biomolecules, a virus, a cell, or a synthetic molecule.

* * * * *

UNITED STATES PATENT AND TRADEMARK OFFICE
CERTIFICATE OF CORRECTION

PATENT NO. : 7,745,220 B2 Page 1 of 1
APPLICATION NO. : 11/542432
DATED : June 29, 2010
INVENTOR(S) : Nicholas Abbott et al.

It is certified that error appears in the above-identified patent and that said Letters Patent is hereby corrected as shown below:

Column 4, line 33 "with three substrates" should be -- with three substrates; C, orientation of LCs in contact with EGX SAMs supported on obliquely deposited gold. --

Signed and Sealed this

Thirty-first Day of August, 2010

David J. Kappos
*Director of the United States Patent and Trademark Office*